(12) United States Patent
VanScoy et al.

(10) Patent No.: US 9,131,982 B2
(45) Date of Patent: Sep. 15, 2015

(54) MEDIGUIDE-ENABLED RENAL DENERVATION SYSTEM FOR ENSURING WALL CONTACT AND MAPPING LESION LOCATIONS

(71) Applicant: St. Jude Medical, Cardiology Division, Inc., St. Paul, MN (US)

(72) Inventors: John VanScoy, Plymouth, MN (US); Ryan Sefkow, Carver, MN (US); Stuart Rosenberg, Castaic, CA (US); Allen Keel, San Francisco, CA (US); Riddhi Shah, San Jose, CA (US); Wenbo Hou, Valencia, CA (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 254 days.

(21) Appl. No.: 13/829,310

(22) Filed: Mar. 14, 2013

(65) Prior Publication Data
US 2014/0276733 A1     Sep. 18, 2014

(51) Int. Cl.
*A61B 18/18*    (2006.01)
*A61B 18/14*    (2006.01)
(Continued)

(52) U.S. Cl.
CPC .......... *A61B 18/1492* (2013.01); *A61B 18/201* (2013.01); *A61B 18/22* (2013.01); *A61B 2018/0016* (2013.01); *A61B 2018/00267* (2013.01); *A61B 2018/00404* (2013.01); *A61B 2018/00434* (2013.01); *A61B 2018/00511* (2013.01); *A61B 2018/00577* (2013.01); *A61B 2018/1467* (2013.01); *A61B 2019/5251* (2013.01); *A61B 2019/5466* (2013.01)

(58) Field of Classification Search
CPC ............... A61B 18/1492; A61B 18/22; A61B 19/5244; A61B 2018/0016; A61B 2018/00267; A61B 2018/00404; A61B 2018/00511; A61B 2018/00577; A61B 2018/1467; A61B 2019/5251; A61B 18/201; A61B 2018/00434; A61B 2019/5466
USPC .......................................................... 606/41
See application file for complete search history.

(56) References Cited

U.S. PATENT DOCUMENTS

| 3,650,277 A | 3/1972 | Sjostrand et al. |
| 3,657,744 A | 4/1972 | Ersek |

(Continued)

FOREIGN PATENT DOCUMENTS

| DE | 19857887 A1 | 7/2000 |
| DE | 10121210 A1 | 11/2002 |

(Continued)

OTHER PUBLICATIONS

Catheter-implanted prosthetic heart valves, Knudsen, L.L., et al., The International Journal of Artificial Organs, vol. 16, No. 5 1993, pp. 253-262.

(Continued)

*Primary Examiner* — George Manuel
(74) *Attorney, Agent, or Firm* — Armstrong Teasdale LLP

(57) ABSTRACT

An ablation catheter includes an elongated body having a proximal end and a distal end. At least one ablation element is disposed on the body between the proximal end and the distal end and configured to ablate renal tissue to control hypertension. At least one localization sensor is disposed on the body and configured to interact with a magnetic field. The at least one localization sensor aids in determining an appropriate target tissue for ablation.

21 Claims, 10 Drawing Sheets

(51) Int. Cl.
   *A61B 18/00* (2006.01)
   *A61B 19/00* (2006.01)
   *A61B 18/22* (2006.01)
   *A61B 18/20* (2006.01)

(56) References Cited

U.S. PATENT DOCUMENTS

| | | |
|---|---|---|
| 4,275,469 A | 6/1981 | Gabbay |
| 4,491,986 A | 1/1985 | Gabbay |
| 4,658,819 A | 4/1987 | Harris et al. |
| 4,759,758 A | 7/1988 | Gabbay |
| 4,878,906 A | 11/1989 | Lindemann et al. |
| 4,922,905 A | 5/1990 | Strecker |
| 4,994,077 A | 2/1991 | Dobben |
| 5,035,694 A | 7/1991 | Kasprzyk et al. |
| 5,255,679 A | 10/1993 | Imran |
| 5,300,068 A | 4/1994 | Rosar et al. |
| 5,368,591 A | 11/1994 | Lennox et al. |
| 5,387,233 A | 2/1995 | Alferness et al. |
| 5,411,552 A | 5/1995 | Andersen et al. |
| 5,465,717 A | 11/1995 | Imran et al. |
| 5,480,423 A | 1/1996 | Ravenscroft et al. |
| 5,531,779 A | 7/1996 | Dahl et al. |
| 5,598,848 A | 2/1997 | Swanson et al. |
| 5,607,462 A | 3/1997 | Imran |
| 5,628,313 A | 5/1997 | Webster, Jr. |
| 5,676,662 A | 10/1997 | Fleischhacker et al. |
| 5,707,400 A | 1/1998 | Terry, Jr. et al. |
| 5,769,077 A | 6/1998 | Lindegren |
| 5,772,590 A | 6/1998 | Webster, Jr. |
| 5,843,167 A | 12/1998 | Dwyer et al. |
| 5,855,601 A | 1/1999 | Bessler et al. |
| 5,893,885 A | 4/1999 | Webster, Jr. |
| 5,897,553 A | 4/1999 | Mulier et al. |
| 5,935,163 A | 8/1999 | Gabbay |
| 5,954,649 A | 9/1999 | Chia et al. |
| 5,954,719 A | 9/1999 | Chen et al. |
| 5,961,549 A | 10/1999 | Nguyen et al. |
| 6,004,269 A | 12/1999 | Crowley et al. |
| 6,012,457 A | 1/2000 | Lesh |
| 6,016,437 A | 1/2000 | Tu et al. |
| 6,024,740 A | 2/2000 | Lesh et al. |
| 6,073,048 A | 6/2000 | Kieval et al. |
| 6,077,297 A | 6/2000 | Robinson et al. |
| 6,083,257 A | 7/2000 | Taylor et al. |
| 6,090,140 A | 7/2000 | Gabbay |
| 6,096,037 A | 8/2000 | Mulier et al. |
| 6,117,101 A | 9/2000 | Diederich et al. |
| 6,161,543 A | 12/2000 | Cox et al. |
| 6,178,349 B1 | 1/2001 | Kieval |
| 6,200,312 B1 | 3/2001 | Zikorus et al. |
| 6,214,036 B1 | 4/2001 | Letendre et al. |
| 6,216,044 B1 | 4/2001 | Kordis |
| 6,233,491 B1 | 5/2001 | Kordis et al. |
| 6,264,691 B1 | 7/2001 | Gabbay |
| 6,267,783 B1 | 7/2001 | Letendre et al. |
| 6,283,951 B1 | 9/2001 | Flaherty et al. |
| 6,287,608 B1 | 9/2001 | Levin et al. |
| 6,292,695 B1 | 9/2001 | Webster, Jr. et al. |
| 6,322,559 B1 | 11/2001 | Daulton et al. |
| 6,368,348 B1 | 4/2002 | Gabbay |
| 6,419,695 B1 | 7/2002 | Gabbay |
| 6,460,545 B2 | 10/2002 | Kordis |
| 6,468,660 B2 | 10/2002 | Ogle et al. |
| 6,488,702 B1 | 12/2002 | Besselink |
| 6,517,576 B2 | 2/2003 | Gabbay |
| 6,522,926 B1 | 2/2003 | Kieval et al. |
| 6,533,810 B2 | 3/2003 | Hankh et al. |
| 6,582,464 B2 | 6/2003 | Gabbay |
| 6,610,088 B1 | 8/2003 | Gabbay |
| 6,613,045 B1 | 9/2003 | Laufer et al. |
| 6,616,624 B1 | 9/2003 | Kieval |
| 6,623,518 B2 | 9/2003 | Thompson et al. |
| 6,635,054 B2 | 10/2003 | Fjield et al. |
| 6,656,174 B1 | 12/2003 | Hegde et al. |
| 6,669,655 B1 | 12/2003 | Acker et al. |
| 6,685,625 B2 | 2/2004 | Gabbay |
| 6,699,231 B1 | 3/2004 | Sterman et al. |
| 6,719,789 B2 | 4/2004 | Cox |
| 6,730,118 B2 | 5/2004 | Spenser et al. |
| 6,748,255 B2 | 6/2004 | Fuimaono et al. |
| 6,783,556 B1 | 8/2004 | Gabbay |
| 6,790,230 B2 | 9/2004 | Beyersdorf et al. |
| 6,805,131 B2 | 10/2004 | Kordis |
| 6,814,746 B2 | 11/2004 | Thompson et al. |
| 6,830,584 B1 | 12/2004 | Seguin |
| 6,845,267 B2 | 1/2005 | Harrison et al. |
| 6,869,444 B2 | 3/2005 | Gabbay |
| 6,893,460 B2 | 5/2005 | Spenser et al. |
| 6,895,267 B2 * | 5/2005 | Panescu et al. ............... 600/424 |
| 6,908,481 B2 | 6/2005 | Cribier |
| 6,954,977 B2 | 10/2005 | Maguire et al. |
| 6,970,730 B2 | 11/2005 | Fuimaono et al. |
| 7,018,406 B2 | 3/2006 | Seguin et al. |
| 7,025,780 B2 | 4/2006 | Gabbay |
| 7,122,031 B2 | 10/2006 | Edwards et al. |
| 7,137,184 B2 | 11/2006 | Schreck |
| 7,149,574 B2 | 12/2006 | Yun et al. |
| 7,155,284 B1 | 12/2006 | Whitehurst et al. |
| 7,160,322 B2 | 1/2007 | Gabbay |
| 7,162,303 B2 | 1/2007 | Levin et al. |
| 7,245,955 B2 | 7/2007 | Rashidi |
| 7,247,167 B2 | 7/2007 | Gabbay |
| 7,267,686 B2 | 9/2007 | DiMatteo et al. |
| 7,291,146 B2 | 11/2007 | Steinke et al. |
| 7,311,730 B2 | 12/2007 | Gabbay |
| 7,363,076 B2 | 4/2008 | Yun et al. |
| 7,374,573 B2 | 5/2008 | Gabbay |
| 7,381,218 B2 | 6/2008 | Schreck |
| 7,419,486 B2 | 9/2008 | Kampa |
| 7,452,371 B2 | 11/2008 | Pavcnik et al. |
| 7,465,288 B2 | 12/2008 | Dudney et al. |
| 7,468,062 B2 | 12/2008 | Oral et al. |
| 7,481,803 B2 | 1/2009 | Kesten et al. |
| 7,510,572 B2 | 3/2009 | Gabbay |
| 7,524,331 B2 | 4/2009 | Birdsall |
| RE40,816 E | 6/2009 | Taylor et al. |
| 7,585,321 B2 | 9/2009 | Cribier |
| 7,653,438 B2 | 1/2010 | Deem et al. |
| 7,682,390 B2 | 3/2010 | Seguin |
| 7,717,948 B2 | 5/2010 | Demarais et al. |
| 7,731,742 B2 | 6/2010 | Schlick et al. |
| 7,742,795 B2 | 6/2010 | Stone et al. |
| 7,803,185 B2 | 9/2010 | Gabbay |
| 7,846,203 B2 | 12/2010 | Cribier |
| 7,846,204 B2 | 12/2010 | Letac et al. |
| 7,850,685 B2 | 12/2010 | Kunis et al. |
| 7,914,569 B2 | 3/2011 | Nguyen et al. |
| 7,949,407 B2 | 5/2011 | Kaplan et al. |
| D648,854 S | 11/2011 | Braido |
| D652,926 S | 1/2012 | Braido |
| D652,927 S | 1/2012 | Braido et al. |
| D653,341 S | 1/2012 | Braido et al. |
| D653,342 S | 1/2012 | Braido et al. |
| D653,343 S | 1/2012 | Ness et al. |
| D654,169 S | 2/2012 | Braido |
| D654,170 S | 2/2012 | Braido et al. |
| 8,145,316 B2 | 3/2012 | Deem et al. |
| D660,432 S | 5/2012 | Braido |
| D660,433 S | 5/2012 | Braido et al. |
| D660,967 S | 5/2012 | Braido et al. |
| 8,224,416 B2 | 7/2012 | de la Rama et al. |
| 8,343,213 B2 | 1/2013 | Salahieh et al. |
| 8,347,891 B2 | 1/2013 | Demarais et al. |
| 8,442,639 B2 | 5/2013 | Walker et al. |
| 8,454,594 B2 | 6/2013 | Demarais et al. |
| 8,545,495 B2 | 10/2013 | Scheib |
| 2002/0036220 A1 | 3/2002 | Gabbay |
| 2002/0068885 A1 | 6/2002 | Harhen et al. |
| 2002/0120304 A1 | 8/2002 | Mest |
| 2003/0023303 A1 | 1/2003 | Palmaz et al. |
| 2003/0050681 A1 | 3/2003 | Pianca et al. |
| 2003/0050694 A1 | 3/2003 | Yang et al. |
| 2003/0060858 A1 | 3/2003 | Kieval et al. |

(56) References Cited

U.S. PATENT DOCUMENTS

| | | |
|---|---|---|
| 2003/0074039 A1 | 4/2003 | Puskas |
| 2003/0114739 A1 | 6/2003 | Fuimaono et al. |
| 2003/0130726 A1 | 7/2003 | Thorpe et al. |
| 2003/0216792 A1 | 11/2003 | Levin et al. |
| 2003/0233099 A1 | 12/2003 | Danaek et al. |
| 2004/0049262 A1 | 3/2004 | Obermiller et al. |
| 2004/0093075 A1 | 5/2004 | Kuehne |
| 2004/0210304 A1 | 10/2004 | Seguin et al. |
| 2004/0215186 A1 | 10/2004 | Cornelius et al. |
| 2005/0096726 A1 | 5/2005 | Sequin et al. |
| 2005/0137695 A1 | 6/2005 | Salahieh et al. |
| 2005/0137697 A1 | 6/2005 | Salahieh et al. |
| 2005/0256566 A1 | 11/2005 | Gabbay |
| 2005/0288730 A1 | 12/2005 | Deem et al. |
| 2006/0008497 A1 | 1/2006 | Gabbay |
| 2006/0074484 A1 | 4/2006 | Huber |
| 2006/0089678 A1 | 4/2006 | Shalev |
| 2006/0122692 A1 | 6/2006 | Gilad et al. |
| 2006/0149360 A1 | 7/2006 | Schwammenthal et al. |
| 2006/0173532 A1 | 8/2006 | Flagle et al. |
| 2006/0178740 A1 | 8/2006 | Stacchino et al. |
| 2006/0206202 A1 | 9/2006 | Bonhoeffer et al. |
| 2006/0241744 A1 | 10/2006 | Beith |
| 2006/0241745 A1 | 10/2006 | Solem |
| 2006/0259120 A1 | 11/2006 | Vongphakdy et al. |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2007/0010876 A1 | 1/2007 | Salahieh et al. |
| 2007/0027534 A1 | 2/2007 | Bergheim et al. |
| 2007/0043435 A1 | 2/2007 | Seguin et al. |
| 2007/0055358 A1 | 3/2007 | Krolik et al. |
| 2007/0067029 A1 | 3/2007 | Gabbay |
| 2007/0093890 A1 | 4/2007 | Eliasen et al. |
| 2007/0100435 A1 | 5/2007 | Case et al. |
| 2007/0118210 A1 | 5/2007 | Pinchuk |
| 2007/0135875 A1 | 6/2007 | Demarais et al. |
| 2007/0213813 A1 | 9/2007 | Von Segesser et al. |
| 2007/0233228 A1 | 10/2007 | Eberhardt et al. |
| 2007/0244545 A1 | 10/2007 | Birdsall et al. |
| 2007/0244552 A1 | 10/2007 | Salahieh et al. |
| 2007/0288087 A1 | 12/2007 | Fearnot et al. |
| 2008/0021552 A1 | 1/2008 | Gabbay |
| 2008/0039934 A1 | 2/2008 | Styrc |
| 2008/0071369 A1 | 3/2008 | Tuval et al. |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0243245 A1 | 10/2008 | Thambar et al. |
| 2008/0255478 A1 | 10/2008 | Burdette |
| 2008/0255662 A1 | 10/2008 | Stacchino et al. |
| 2008/0262602 A1 | 10/2008 | Wilk et al. |
| 2008/0269879 A1 | 10/2008 | Sathe et al. |
| 2009/0076409 A1 | 3/2009 | Wu et al. |
| 2009/0112309 A1 | 4/2009 | Jaramillo et al. |
| 2009/0138079 A1 | 5/2009 | Tuval et al. |
| 2010/0004740 A1 | 1/2010 | Seguin et al. |
| 2010/0016762 A1 | 1/2010 | Thapliyal et al. |
| 2010/0036484 A1 | 2/2010 | Hariton et al. |
| 2010/0049306 A1 | 2/2010 | House et al. |
| 2010/0087907 A1 | 4/2010 | Lattouf |
| 2010/0094209 A1 | 4/2010 | Drasler et al. |
| 2010/0131055 A1 | 5/2010 | Case et al. |
| 2010/0168737 A1 | 7/2010 | Grunewald |
| 2010/0168778 A1 | 7/2010 | Braido |
| 2010/0168839 A1 | 7/2010 | Braido et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0249773 A1 | 9/2010 | Clark et al. |
| 2010/0249911 A1 | 9/2010 | Alkhatib |
| 2010/0249923 A1 | 9/2010 | Alkhatib et al. |
| 2010/0268307 A1 | 10/2010 | Demarais et al. |
| 2010/0286684 A1 | 11/2010 | Hata et al. |
| 2010/0286768 A1 | 11/2010 | Alkhatib |
| 2010/0298931 A1 | 11/2010 | Quadri et al. |
| 2011/0004087 A1 | 1/2011 | Fish et al. |
| 2011/0029072 A1 | 2/2011 | Gabbay |
| 2011/0118726 A1 | 5/2011 | de la Rama et al. |
| 2011/0137298 A1 | 6/2011 | Nguyen et al. |
| 2011/0160720 A1 | 6/2011 | Johnson |
| 2011/0213231 A1 | 9/2011 | Hall et al. |
| 2011/0257641 A1 | 10/2011 | Hastings et al. |
| 2011/0264011 A1 | 10/2011 | Wu et al. |
| 2011/0264086 A1 | 10/2011 | Ingle |
| 2012/0143097 A1 | 6/2012 | Pike, Jr. |
| 2012/0143298 A1 | 6/2012 | Just et al. |
| 2012/0296232 A1 | 11/2012 | Ng |
| 2012/0323233 A1 | 12/2012 | Maguire et al. |
| 2013/0116737 A1 | 5/2013 | Edwards et al. |
| 2013/0131743 A1 | 5/2013 | Yamasaki et al. |
| 2013/0144251 A1 | 6/2013 | Sobotka |
| 2013/0172715 A1 | 7/2013 | Just et al. |

FOREIGN PATENT DOCUMENTS

| | | |
|---|---|---|
| DE | 202008009610 U1 | 12/2008 |
| EP | 0850607 A1 | 7/1998 |
| EP | 1000590 A1 | 5/2000 |
| EP | 1360942 A1 | 11/2003 |
| EP | 1584306 A1 | 10/2005 |
| EP | 1598031 A2 | 11/2005 |
| FR | 2847800 A1 | 6/2004 |
| FR | 2850008 A1 | 7/2004 |
| WO | 9117720 A1 | 11/1991 |
| WO | 9716133 A1 | 5/1997 |
| WO | 97/45157 | 12/1997 |
| WO | 9832412 A2 | 7/1998 |
| WO | 9913801 A1 | 3/1999 |
| WO | 00/66020 | 11/2000 |
| WO | 01/00273 | 1/2001 |
| WO | 01/22897 | 4/2001 |
| WO | 0128459 A1 | 4/2001 |
| WO | 0149213 A2 | 7/2001 |
| WO | 0154625 A1 | 8/2001 |
| WO | 0156500 A2 | 8/2001 |
| WO | 0176510 A2 | 10/2001 |
| WO | 02/26314 | 4/2002 |
| WO | 0236048 A1 | 5/2002 |
| WO | 0247575 A2 | 6/2002 |
| WO | 03047468 A1 | 6/2003 |
| WO | 03/082080 | 10/2003 |
| WO | 2006/041881 | 4/2006 |
| WO | 2006073626 A2 | 7/2006 |
| WO | 2007071436 A2 | 6/2007 |
| WO | 2007/149970 | 12/2007 |
| WO | 2008070797 A2 | 6/2008 |
| WO | 2008/141150 | 11/2008 |
| WO | 2008/151001 | 12/2008 |
| WO | 2010008548 A2 | 1/2010 |
| WO | 2010008549 A1 | 1/2010 |
| WO | 2010096176 A1 | 8/2010 |
| WO | 2010098857 A1 | 9/2010 |
| WO | 2012/064818 | 5/2012 |
| WO | 2012/106492 | 8/2012 |

OTHER PUBLICATIONS

Is It Reasonable to Treat All Calcified Stenotic Aortic Valves With a Valved Stent?, 579-584, Zegdi, Rachid, MD, PhD et al., J. of the American College of Cardiology, vol. 51, No. 5, Feb. 5, 2008.

Quaden et al., "Percutaneous aortic valve replacement: resection before implantation", pp. 836-840, European J. of Cardio-thoracic Surgery, 27 (2005).

Ruiz, Carlos, Overview of PRE-CE Mark Transcatheter Aortic Valve Technologies, Euro PCR, dated May 25, 2010.

(56) References Cited

OTHER PUBLICATIONS

Transluminal Aortic Valve Placement, Moazami, Nader, et al., ASAIO Journal, 1996; 42:M381-M385.
Transluminal Catheter Implanted Prosthetic Heart Valves, Andersen, Henning Rud, International Journal of Angiology 7:102-106 (1998).
Transluminal implantation of artificial heart valves, Andersen, H. R., et al., European Heart Journal (1992) 13, 704-708.
U.S. Appl. No. 29/375,243 filed on Sep. 20, 2010.
U.S. Appl. No. 29/375,260 filed on Sep. 20, 2010.
Dibona, Gerald H, Renal Innervation and Denervation: Lessons from Renal Transplantation Reconsidered, Artificial Organs, vol. 11, No. 6, 1987, 457-462.
Dibona, Gerald F., Role of the Renal Nerves in Renal Sodium Retention and Edema Formation, Trans Am Clin Climatol Assoc. 1990; 101: 38-45.
Dibona, Gerald F., Sympathetic Nervous System and Hypertension, Hypertension Journal of the American Heart Association, 2013; 61: 556-560.
Dibona, Gerald F., Sympathetic Nervous System and the Kidney in Hypertension, Curr Opin Nephrol Hypertens. Mar. 2002;11(2):197-200.
Dibona, Gerald F., The Sympathetic Nervous System and Hypertension, Hypertension Journal of the American Heart Association, Vo. 43, Feb. 2004, 147-150.
Doumas, Michael et al, Interventional Management of Resistant Hypertension, The Lancet, vol. 373, Apr. 11, 2009, pp. 1228-1230.
Dubuc, Marc et al, Feasibility of Cardiac Cryoablation Using a Transvenous Steerable Electrode Catheter, Journal of Interventional Cardiac Electrophysiology, 1998, 2: 285-292.
Elmula, Fadl et al, Renal Sympathetic Denervation in Patients With Treatment-Resistant Hypertension After Witnessed Intake of Medication Before Qualifying Ambulatory Blood Pressure, Hypertension. 2013;62:526-532.
Esler, M. et al, Sympathetic Nerve Activity and Neurotransmitter Release in Humans: Translation from Pathophysiology into Clinical Practice, Scandinavian Physiological Society, 2003, 177, 275-284.
Esler, Murray D. et al, Renal Sympathetic Denervation in Patients with Treatment-Resistant Hypertension (The Symplicity HTN-2 Trial): A Randomised Controlled Trial, Lancet, 2010; 376:1903-1909.
Esler, Murray et al, Assessment of Human Sympathetic Nervous System Activity from Measurements of Norepinephrine Turnover, Hypertension Journal of the American Heart Association, vol. 11, No. 1, Jan. 1988, 3-20.
Evelyn, Kenneth A. et al, Effect of Thoracolumbar Sympathectomy on the Clinical Course of Primary (Essential) Hypertension, American Journal of Medicine, Feb. 1960, 188-221.
Freyberg, R. H. et al, The Effect on the Kidney of Bilateral Splanchnicectomy in Patients with Hypertension, The Journal of Clinical Investigation, vol. 16, Issue 1, Jan. 1937, 49-65.
Gafoor, Sameer et al, Nonresponders to Renal Denervation for Resistant Hypertension, Endovascular Today, Oct. 2013, 63-70.
Garel, L. et al, Fatal Outcome After Ethanol Renal Ablation in Child with End-Stage Kidneys; AJR 146:593-594, Mar. 1986.
Gazdar, A. F. et al, Neural Degeneration and Regeneration in Human Renal Transplants, The New England Journal of Medicine, vol. 238, No. 5, Jul. 1970, 222-224.
Goldberg, Michael R. et al, Reconstructive Vascular Surgery for Renovascular Hypertension, Can Med Assoc J. Feb. 2, 1974;110(3):275-80.
Golwyn, Daniel H. et al, Percutaneous Transcatheter Renal Ablation with Absolute Ethanol for Uncontrolled Hypertension or Nephrotic Syndrome: Results in 11 Patients with End-Stage Renal Disease, Journal of Vascular and Interventional Radiology, Jul.-Aug. 1997, vol. 8, No. 4, 527-533.
Gorisch, Wolfram et al, Heat-Induced Contraction of Blood Vessels, Lasers in Surgery and Medicine 2:1-13 (1982).
Grassi, Guido et al, Baroreflex Control of Sympathetic Nerve Activity in Essential and Secondary Hypertension, Hypertension Journal of The American Heart Association, 1998;31:68-72.
Grassi, Guido et al, Dissociation Between Muscle and Skin Sympathetic Nerve Activity in Essential Hypertension, Obesity, and Congestive Heart Failure, Hypertension. 1998;31:64-67.
Grimson, Keith S. et al, Results of Treatment of Patients with Hypertension by Total Thoracic and Partial to Total Lumbar Sympathectomy, Splanchnicectomy and Celiac Ganglionectomy, Annals of Surgery, Jun. 1949, vol. 129, No. 6, 850-871.
Grimson, Keith S. et al, Total Thoracic and Partial to Total Lumbar Sympathectomy, Splanchnicectomy and Celiac Ganglionectomy for Hypertension, Annals of Surgery, Oct. 1953, vol. 138, No. 4, 532-547.
Grimson, Keith S., Total Thoracic and Partial to Total Lumbar Sympathectomy and Celiac Ganglionectomy in the Treatment of Hypertension, Annals of Surgery, Oct. 1941, vol. 114, No. 4, 753-775.
Guyton, Arthur C., Blood Pressure Control Special Role of the Kidneys and Body Fluids, Science, vol. 252, Jun. 1991, 1813-1816.
Hafkenschiel, Joseph H. et al, Primary Hypertension Survey of the Survival of Patients with Established Diastolic Hypertension After Ten Years of Medical and Surgical Treatment, The American Journal of Cardiology, vol. 16, Jul. 1965, 61-66.
Hafkenschiel, Joseph H. et al, the Surgical Treatment of Hypertension with Particular Reference to Andrenalectomy and Sympathectomy, Transactions. American College of Cardiology, vol. 5, Dec. 1955, pp. 107-112.
Hall, J.E. et al, Role of Sympathetic Nervous System and Neuropeptides in Obesity Hypertension, Brazilian Journal of Medical and Biological Research, 2000, 33:605-618.
Hall, John E., The Kidney, Hypertension, and Obesity, Hypertension. 2003;41:625-633.
Hall, Winthrop H. et al, Combined Embolization and Percutaneous Radiofrequency Ablation of a Solid Renal Tumor, American Journal of Roentgenology, 174, Jun. 2000, 1592-1594.
Hamm, Christian et al, Confluence, Issue eight, Apr. 2014.
Han, Young-Min et al, Renal Artery Embolization with Diluted Hot Contrast Medium: An Experimental Study, Journal of Vascular and Interventional Radiology, Jul. 2001;12(7):862-868.
Hansen, Jesper Melchoir et al, The Transplanted Human Kidney Does Not Achieve Functional Reinnervation, Clinical Science, (1994) 87, 13-20.
Heuer, George J., The Surgical Treatment of Essential Hypertension, Annals of Surgery, Oct. 1936, vol. 104, No. 3, 771-786.
Hinton, J. William, End Results of Thoracolumbar Sympathectomy for Advanced Essential Hypertension, The Bulletin, Apr. 1948, 239-252.
Holmer, Stephan et al, Role of Renal Nerves for the Expression of Renin in Adult Rat Kidney, The American Journal of Physiology, May 1994;266(5 Pt 2):F738-F745.
Hoobler, S.W. et al, The Effects of Splanchnicectomy on the Blood Pressure in Hypertension, Circulation Journal of The American Heart Association, vol. IV, Aug. 1951, 173-183.
Hoppe, Uta C. et al, Minimally Invasive System for Baroreflex Activation Therapy Chronically Lowers Blood Pressure with Pacemaker-like Safety Profile: Results from the Barostim Neo Ttrial, J Am Soc Hypertens. Jul.-Aug. 2012;6 (4):270-6.
Howard, James P. et al, Size of Blood Pressure Reduction from Renal Denervation: Insights from Meta-Analysis of Antihypertensive Drug Trials of 4121 Patients with Focus on Trial Design: The Converge Report, Heart 2013;0:1-9.
Howard, James P. et al, Unintentional Overestimation of an Expected Antihypertensive Effect in Drug and Device Trials: Mechanisms and Solutions, International Journal of Cardiology, vol. 172, Issue 1, Mar. 1, 2014, pp. 29-35.
Howell, Marcus H. et al, Tandem Stenting of Crossed Renal Arteries with Ostial Stenosis, Tex Heart Inst J. 2000; 27(2): 166-169.
Hoye, Neil A. et al, Endovascular Renal Denervation: A Novel Sympatholytic with Relevance to Chronic Kidney Disease, Clinical Kidney Journal Advance Access, (2013) 0: 1-8.
Huang, Shoei K. Stephen et al, Radiofrequency Catheter Ablation of Cardiac Arrhythmias, Basic Concepts and Clinical Applications, Wiley-Blackwell, Jun. 1-12, 2000.

(56) References Cited

OTHER PUBLICATIONS

Huang, Wann-Chu, Renal Denervation Prevents and Reverses Hyperinsulinemia-Induced Hypertension in Rats, Hypertension Journal of the American Heart Association, 1998;32:249-254.
Humpreys, Michael H., Renal Nerves and CKD: Is Renal Denervation the Answer?, Journal of the American Socity of Nephrology, 2012, 23: 1-3.
International Search Report and Written Opinion for Application No. PCT/US2010/054637 mailed Jan. 3, 2011.
International Search Report and Written Opinion for Application No. PCT/US2010/054684 mailed Jan. 10, 2011.
Irigoyen, M.C.C. et al, Baroreflex Control of Sympathetic Activity in Experimental Hypertension, Brazilian Journal of Medical and Biological Research, (1998) 31: 1213-1220.
Izzo, Jr., Joseph L. et al, The Sympathetic Nervous System and Baroreflexes in Hypertension and Hypotension, Current Hypertension Reports 1999, 3:254-263.
Jackman, Warren M. et al, Catheter Ablation of Arrhythmias, Proposed Anatomy and Catheter Ablation of Epicardial Posteroseptal and Left Posterior Accessory AV Pathways (Chapter 16), 2002, Futura Publishing Company, Inc., 321-343.
Robbins, Ivan M. et al, Pulmonary Vein Stenosis After Catheter Ablation of Atrial Fibrillation, Circulation Journal of The American Heart Association, 1998;98:1769-1775.
Rocha-Singh, Krishna J., Catheter-Based Sympathetic Renal Denervation A Novel Strategy for the Treatment of Resistant Hypertension, Endovascular Today, Aug. 2009, 52-56.
Rocha-Singh, Krishna J., Renal Artery Denervation: A Brave New Frontier, Endovascular Today, Feb. 2012, 45-53.
Sanderson, John E. et al, Effect of B-Blockade on Baroreceptor and Autonomic Function in Heart Failure, Clinical Science (1999) 96, 137-146.
Santos, Mario et al, Renal Sympathetic Denervation in Resistant Hypertension, World J Cardiol Apr. 26, 2013; 5(4): 94-101.
Savard, Sebastien et al, Eligibility for Renal Denervation in Patients With Resistant Hypertension When Enthusiasm Meets Reality in Real-Life Patients, J Am Coll Cardiol. 2012;60(23):2422-2424.
Schauerte, Patrick et al, Catheter Ablation of Cardiac Autonomic Nerves for Prevention of Vagal Atrial Fibrillation, Circulation Journal of the American Heart Association, 2000, 102:2774-2780.
Schlaich, Markus P. et al, International Expert Consensus Statement: Percutaneous Transluminal Renal Denervation for the Treatment of Resistant Hypertension, Journal of the American College of Cardiology vol. 62, Issue 22, Dec. 3, 2013, pp. 2031-2045.
Schlaich, Markus P. et al, Renal Denervation as a Therapeutic Approach for Hypertension Novel Implications for an Old Concept, Hypertension Journal of The American Heart Association, 2009;54:1195-1201.
Schlaich, Markus P. et al, Renal Sympathetic-Nerve Ablation for Uncontrolled Hypertension, The New England Journal of Medicine, 2009; 361:932-934.
Schmieder, Roland E. et al, ESH Position Paper: Renal Denervation—An Iterventional Therapy of Resistant Hypertension, Journal of Hypertension, 2012, 30:837-841.
Schmieder, Roland E. et al, Updated EHS Position Paper on Interventional Therapy of Resistant Hypertension, EuroIntervention 2013; 9:R58-R66.
Sellers, Alfred M. et al, Adrenalectomy and Sympathectomy for Hypertension Ten Year Survival, Archives of Surgery, vol. 89, Nov. 1964, 880-886.
Sen, S.K., Some Observations on Decapsulation and Denervation of the Kidney, The British Journal of Urology, vol. 8, Issue 4, Dec. 1936, 319-328.
Shiraki, Iwao William, Correction of Renal Hypertension by Ligation of Stenotic Segmental Renal Artery, Urology, vol. IX, No. 3, Mar. 1977, 296-298.
Shonai, Takaharu et al, Renal Artery Aneurysm: Evaluation with Color Doppler Ultrasonography Before and After Percutaneous Transarterial Embolization, J Ultrasound Med 19:277-280, 2000.
Silver, Donald et al, Renovascular Hypertension From Renal Artery Compression by Congenital Bands, Annals of Surgery, Feb. 1976, 161-166.
Smith, Gardner W. et al, Surgical Results and the Diagnostic Evaluation of Renovascular Hypertension, Annals of Surgery, May 1968, 669-680.
Smith, Harold P. et al, Radiofrequency Neurolysis in a Clinical Model Neuropathological Correlation, J Neurosurg 55:246-253, 1981.
Smithwick, R.H., An Evaluation of the Surgical Treatment of Hypertension, The Bulletin, Nov. 1949; 25(11):698-716.
Smithwick, Reginald H. et al, Splanchnicectomy for Essential Hypertension, The Journal of the American Medical Association, vol. 152, No. 16, Aug. 1953, 1501-1504.
Solis-Herruzo, J.A. et al, Effects of Lumbar Sympathetic Block on Kidney Function in Cirrhotic Patients with Hepatorenal Syndrome, Journal of Hepatology, 1987; 5: 167-173.
Sowers, James R. et al, Diabetes, Hypertension, and Cardiovascular Disease: An Update, Hypertension Journal of The American Heart Association, 2001;37:1053-1059.
Stanley, James C., Surgical Treatment of Renovascular Hypertension, The American Journal of Surgery, vol. 174, Aug. 1997, 102-110.
Stella, Andrea et al, Effects of Reversible Renal Denervation on Haemodynamic and Excretory Functions of the Ipsilateral and Contralateral Kidney in the Cat, Journal of Hypertension 1986, 4: 181-188.
Stuart, Candace, Newest Frontier in Cardiac Care: Kidneys; Cardiovascular Business, Dec. 13, 2012.
Stuart, Mary, Masterminds of Ardian: An Interview With Inventors Mark Gelfand and Howard Levin, Windhover Information, Start-Up Jan. 1, 2011.
Sun, Yingxian et al, Risk of Coronary Stenosis with Venous Ablation for Epicardial Accessory Pathways, Pace, Apr. 2001, Part II, vol. 24, 605.
Swartz, John F. et al, Radiofrequency Endocardial Catheter Ablation of Accessory Atrioventricular Pathway Atrial Insertion Sites, Circulation Journal of the American Heart Association, 1993;87:487-499.
Teigen, Corey L. et al, Segmental Renal Artery Embolization for Treatment of Pediatric Renovascular Hypertension, Journal of Vascular and Interventional Radiology, 1992; 3:111-117.
Teixeira, Maria Do Carmo et al,1992; Role of the Peripheral Renin Profile in Predicting Blood Pressure Control After Bilateral Nephrectomy in Renal-Transplanted Patients, Nephrol Dial Transplant (1998) 13: 2092-2097.
Teo, W S et al, Radiofrequency Catheter Ablation of Accessory Pathways: The Initial Experience in Singapore, . Singapore Medical Journal, 1994; vol. 35:36-40.
Thiebot, J. et al, Bilateral Nephrectomy by Embolization of the Renal Arteries: A Report on Five Cases (author's transl), Sem Hop. Apr. 8-15, 1980;56(13-14):670-5.
Thomas, George et al, Renal Denervation to Treat Resistant Hypertension: Guarded Optimism, Cleveland Clinic Journal of Medicine, vol. 79, No. 7, Jul. 2012, 501-510.
Thomas, Natalie A., Secondary Consideration in Nonobviousness Analysis: The Use of Objective Indicia Following KSR V. Teleflex, NYU Law Review, vol. 86, No. 6, Dec. 2011, 2070-2112.
Ting, Chih-Tai et al, Arterial Hemodynamics in Human Hypertension Effects of Angiotensin Converting Enzyme Inhibition, Hypertension Journal of the American Heart Association, 1993;22:839-846.
Uchida, Fumiya et al, Effect of Radiofrequency Catheter Ablation on Parasympathetic Denervation: A Comparison of Three Different Ablation Sites, Pace, vol. 21, Nov. 1998, Part II, 2517-2521.
Valente, John F. et al, Laparoscopic Renal Denervation for Intractable Adpkd-Related Pain, Nephrol Dial Transplant (2001) 16:160.
Villarreal, Daniel et al, Effects of Renal Denervation on Postprandial Sodium Excretion in Experimental Heart Failure, American Journal of Physiology, May 1994;266(5 Pt 2):R1599-R1604.
Von End, Oliver et al, Secondary Rise in Blood Pressure After Renal Denervation, The Lancet, vol. 380, Issue 9843, p. 778, Aug. 25, 2012.
Vujaskovic, Z. et al, Effects of Intraoperative Hyperthermia on Canine Sciatic Nerve: Histopathologic and Morphometric Studies, Int. J. Hyperthermia, 1994, vol. 10, No. 6, 845-855.

(56) References Cited

OTHER PUBLICATIONS

Webb, R.L. et al, Functional Identification of the Central Projections of Afferent Renal Nerves, Clin. And Exper.- Theory and Practice, Ag(Suppl.I), 47-57 (1987).
Weinstock, Marta et al, Renal Denervation Prevents Sodium Retention and Hypertension in Salt-Sensitive Rabbits with Genetic Baroreflex Impairment, Clinical Science (1996) 90, 287-293.
Wilcox, Josiah N., Scientific Basis Behind Renal Denervation for the Control of Hypertension, Medtronic, Inc., Dec. 2012, 38 pages.
Winternitz, Sherry R. et al, Role of the Renal Sympathetic Nerves in the Development and Maintenance of Hypertension in the Spontaneously Hypertensive Rat, Journal of Clinical Investigation, vol. 66 Nov. 1980, 971-978.
Wolf-Maier, Katharina et al, Hypertension Treatment and Control in Five European Countries, Canada, and the United States, Hypertension. 2004;43:10-17.
Worthley, Stephen G. et al, Renal Denervation: How Do You Measure Success?, presentation 28 pages; Jul. 30, 2013.
Wyss, J.M. et al, Sensory Denervation of the Kidney Attenuates Renovascular Hypertension in the Rat, Am J Physiol Heart Circ Physiol 250:H82-H86, 1986.
Yamada, Yutaka et al, Age-Related Changes in Muscle Sympathetic Nerve Activity in Essential Hypertension, Hypertension Journal of the American Heart Association, 1989;13:870-877.
Young, Robert R. et al, Reversible Block of Nerve Conduction by Ultrasound Ultrasonic Blocking of Nerve Fibers, Arch Neurol. 1961;4(1):83-89.
Abboud, Francois M., The Sympathetic System in Hypertension, State-of-the-Art Review, Hypertension Journal of the American Heart Association, Hypertension 4 (suppl II): II-208-II-225, 1982.
Allen, Edgar V., Sympathectomy for Essential Hypertension, Circulation Journal of the American Heart Association, vol. VI, Jul. 1952, 131-140.
Anderson, Erling A. et al, Elevated Sympathetic Nerve Activity in Borderline Hypertensive Humans, Evidence From Direct Intraneural Recordings, Hypertension Journal of the American Heart Association, vol. 14, No. 2, Aug. 1989, 177-183.
Ardian, Inc., Ardian(R) Receives 2010 EuroPCR Innovation Award and Demonstrates Further Durability of Renal Denervation Treatment for Hypertension, PR Newswire, Jun. 3, 2010.
Arentz, Thomas et al, Feasibility and Safety of Pulmonary Vein Isolation Using a New Mapping and Navigation System in Patients with Refractory Atrial Fibrillation, Circulation Journal of the American Heart Association, Nov. 18, 2003, 2484-2490.
Badoer, Emilio et al, Cardiac Afferents Play the Dominant Role in Renal Nerve Inhibition Elicited by Volume Expansion in the Rabbit, American Journal of Physiology, 1998, R383-R388.
Bakris, George L. et al, Baroreflex Activation Therapy Provides Durable Benefit in Patients with Resistant Hypertension: Results of Long-Term Follow-up in the Rheos Pivotal Trial, J Am Soc Hypertens. Mar.-Apr. 2012;6 (2):152-8.
Bao, Gang et al, Blood Pressure Response to Chronic Episodic Hypoxia: Role of the Sympathetic Nervous System, American Journal of Physiology, 1997, 95-101.
Barajas, Luciano et al, Anatomy of the Renal Innervation: Intrarenal Aspects and Ganglia of Origin, Canadian Journal of Physiology and Pharmacology, vol. 70, No. 5, May 1992, 735-749.
Barajas, Luciano et al, Monoaminergic Innervation of the Rat Kidney: A Quantitative Study, American Journal of Physiology, vol. 259, No. 3, Sep. 1990, F503-F511.
Bardram, Linda et al, Late Results After Surgical Treatment of Renovascular Hypertension, A Follow-up Study of 122 Patients 2-18 Years After Surgery, Annals of Surgery, vol. 201, No. 2, Feb. 1985, 219-224.
Bello-Reuss, Elsa et al, Effect of Renal Sympathetic Nerve Stimulation on Proximal Water and Sodium Reabsorption, The Journal of Clinical Investigation, vol. 57, Apr. 1976, 1104-1107.
Bello-Reuss, Elsa et al, Effects of Acute Unilateral Renal Denervation in the Rat, The Journal of Clinical Investigation, vol. 56, Jul. 1975, 208-217.

Benito, Fernando et al, Radiofrequency Catheter Ablation of Accessory Pathways in Infants, Heart, 1997, 78, 160-162.
Bernardi, Luciano et al, Influence of Type of Surgery on the Occurrence of Parasympathetic Reinnervation After Cardiac Transplantation, Circulation Journal of the American Heart Association, Apr. 14, 1998;97(14):1368-74.
Bertog, Stefan C. et al, Renal Denervation for Hypertension, JACC: Cardiovascular Interventions, vol. 5, No. 3, Mar. 2012, 249-258.
Bertram, Harald et al, Coronary Artery Stenosis After Radiofrequency Catheter Ablation of Accessory Atrioventricular Pathways in Children with Ebstein's Malformation, Circulation Journal of the American Heart Association, 2001, 538-543.
Blankestijn, Peter J. et al, Renal Denervation: Potential Impact on Hypertension in Kidney Disease?, Nephrol Dial Transplant (2011) 0: 1-3.
Blankestijn, Peter J. et al, Sympathetic Overactivity in Renal Failure Controlled by ACE Inhibition: Clinical Significance, Nephrol Dial Transplant, 2000, 15, 755-758.
Blum, Ulrich et al, Treatment of Ostial Renal-Artery Stenoses with Vascular Endoprostheses After Unsuccessful Balloon Angioplasty, The New England Journal of Medicine, vol. 336, No. 7, Feb. 1997, 459-465.
Brinkmann, Julia et al, Catheter-Based Renal Nerve Ablation and Centrally Generated Sympathetic Activity in Difficult-to-Control Hypertensive Patients Prospective Case Series, Hypertension. 2012;60:1485-1490.
Brookes, Linda et al, Renal Denervation: Is Reality Meeting Expectations?, An Interview with Michel Azizi, MD, PhD, Medscape, Jan. 7, 2013.
Bunte, Matthew C. et al, Endovascular Treatment of Resistant and Uncontrolled Hypertension, JACC: Cardiovascular Interventions, vol. 6, No. 1, 2013, 1-9.
Calleary, Hickey D. et al, Pre-Transplant Bilateral Native Nephrectomy for Medically Refractory Hypertension, The Irish Medical Journal, Jul.-Aug. 2001;94(7):214-6.
Callens, David J. et al, Narrowing of the Superior Vena Cava-Right Atrium Junction During Radiofrequency Catheter Ablation for Inappropriate Sinus Tachycardia: Analysis with Intracardiac Echocardiography, Journal of the American College of Cardiology, vol. 33, No. 6, 1999, 1667-1670.
Campese, V.M., Is Hypertension in Chronic Renal Failure Neurogenic in Nature?, Nephrol Dial Transplant, 1994, 9: 741-742.
Campese, Vito M. et al, Neurogenic Factors in Renal Hypertension, Current Hypertension Reports, 2002 4: 256-260.
Campese, Vito M. et al, Renal Afferent Denervation Prevents Hypertension in Rats With Chronic Renal Failure, Hypertension, 1995, 25, 878-882.
Campese, Vito M. et al, Renal Afferent Denervation Prevents the Progression of Renal Disease in the Renal Ablation Model of Chronic Renal Failure in Rat, American Journal of Kidney Disease, vol. 26, No. 5, Nov. 1995, 861-865.
Campese, Vito M., Interventional Hypertension: A New Hope or a New Hype? The Need to Redefine Resistant Hypertension, J Hypertens. Nov. 2013;31(11):2118-21.
Canadian Agency for Drugs and Technologies in Health, Catheter-Based Renal Denervation for Treatment-Resistant Hypertension; Issues in Emerging Health Technologies, Issue 121, Mar. 2013.
Carlstedt, Thomas et al, Regrowth of Lesioned Dorsal Root Nerve Fibers into the Spinal Cord of Neonatal Rats, Neuroscience Letters Feb. 10, 1987;74(1)14-8.
Chabanier, H. et al, On the Decapsulation and Neurectomy of the Kidnesy in Permanent Hypertensive States, The Medical Press, Feb. 22, 1936, No. 16, 307-310.
Ciccone, C D et al, Effects of Acute Renal Denervation on Kidney Function in Deoxycorticosterone Acetate-Hypertensive Swine, Hypertension Journal of the American Heart Association, Oct. 1986, vol. 8, No. 10, 925-931.
Ciriello, John et al, Renal Afferents and Hypertension, Current Hypertension Reports 2002, 4:136-142.
Converse, Richard L. et al, Sympathetic Overactivity in Patients with Chronic Renal Failure, The New England Journal of Medicine, vol. 327, No. 27, 1992, 1912-1918.

(56) References Cited

OTHER PUBLICATIONS

Crile, George, The Clinical Results of Celiac Ganglionectomy in the Treatment of Essential Hypertension, Annals of Surgery, Jun. 1938; 107(6): 909-916.
Cruickshank, J.M., Beta-Blockers Continue to Surprise Us, European Heart Journal (2000) 21, 354-364.
Curtis, John J. et al, Surgical Therapy for Persistent Hypertension After Renal Transplantation, Transplantation, vol. 31, No. 2, 1981, 125-128.
Dailey, U.G., Surgical Treatment of Hypertension: A Review-Part II, Journal of the National Medical Association, May 1948, vol. 40, No. 3., 113-116.
Dailey, U.G., Surgical Treatment of Hypertension: A Review-Part III, Journal of the National Medical Association, Jul. 1948, vol. 40, No. 4, 160-162.
Dailey, U.G., The Surgical Treatment of Hypertension: A Review, Journal of the National Medical Association, Mar. 1948, vol. 40, No. 2, 76-79.
Davis, Mark I. et al, Effectiveness of Renal Denervation Therapy for Resistant Hypertension a Systematic Review and Meta-Analysis, Journal of the American College of Cardiology, vol. 62, No. 3, 2013, 231-241.
De Wardener, H.E., The Hypothalamus and Hypertension, Physiological Reviews, vol. 81, No. 4, Oct. 2001.
Dequattro V. et al, The Sympathetic Nervous System: The Muse of Primary Hypertension, Journal of Human Hypertension, 2002, 16 (Suppl 1), S64-S69.
Dibona, Gerald F. et al, Neural Control of Renal Function, Physiological Reviews, vol. 77, No. 1, Jan. 1997, 75-197.
Dibona, Gerald F. et al, Translational Medicine: The Antihypertensive Effect of Renal Denervation, Americal Journal of Physiology, 2010, 298, R245-R253.
Dibona, Gerald F., Neural Control of Renal Function: Cardiovascular Implications, Hypertension Journal of the American Heart Association, vol. 13, No. 6, Part 1, Jun. 1989, 539-548.
Dibona, Gerald F., Neural Control of the Kidney: Functionally Specific Renal Sympathetic Nerve Fibers, American Journal of Physiology, 2000, 279, R1517-R1524.
Dibona, Gerald F., Neural Control of the Kidney: Past, Present, and Future, Hypertension Journal of the American Heart Association, vol. 41, Mar. 2003, Part II, 621-624.
Moak, Jeffrey P. et al, Case Report: Pulmonary Vein Stenosis Following RF Ablation of Paroxysmal Atrial Fibrillation: Successful Treatment with Balloon Dilation, Journal of Interventional Cardiac Electrophysiology, Dec. 4, 2000, 4:621-631.
Mogil, Robert A. et al, Renal Innervation and Renin Activity in Salt Metabolism and Hypertension, American Journal of Physiology, vol. 216, No. 4, Apr. 1969, 693-697.
Morita, Hironobu et al, Neural Control of Urinary Sodium Excretion During Hypertonic NaC1 Load in Conscious Rabbits: Role of Renal and Hepatic Nerves and Baroreceptors, Journal of the Autonomic Nervous System, 34 (1991).
Morrissey, D.M. et al, Sympathectomy in the Treatment of Hypertension, The Lancet, Feb. 1953, 403-408.
Mortara, Andrea et al, Nonselective Beta-Adrenergic Blocking Agent, Carvedilol, Improves Arterial Baroflex Gain and Heart Rate Variability in Patients With Stable Chronic Heart Failure, Journal of the American College of Cardiology, vol. 36, No. 5, 2000, 1612-1618.
Moss, Jonathan, Interventional Radiology and Renal Denervation, Interventions, vol. 13, Issue 3, 2013.
Naghavi, Morteza et al, Thermography Basket Catheter: In Vivo Measurement of the Temperature of Atherosclerotic Plaques for Detection of Vulnerable Plaques, Catheterization and Cardiovascular Interventions 59:5259 (2003).
Naidoo, N. et al, Thoracic Splanchnic Nerves: Implications for Splanchnic Denervation, Journal of Anatomy, Nov. 2001;199(Pt 5):585-590.
Nakagawa, A. et al, Selective Ablation of Porcine and Rabbit Liver Tissue Using Radiofrequency: Preclinical Study, European Surgical Research, 1999;31:371-379.
Nakagawa, Hiroshi et al, Inverse Relationship Between Electrode Size and Lesion Size During Radiofrequency Ablation With Active Electrode Cooling, Circulation. Aug. 4, 1998;98(5):458-465.
Nanni, Gregg S. et al, Control of Hypertension by Ethanol Renal Ablation, Radiology 148: 51-54, Jul. 1983.
Ndegwa, S., Catheter-Based Renal Denervation for Treatment-Resistant Hypertension [Issues in emerging health technologies issue 121]. Ottawa: Canadian Agency for Drugs and Technologies in Health; 2013.
Neutel, Joel M., Hypertension and Its Management: A Problem in Need of New Treatment Strategies, Journal of Renin-Angiotensin-Aldosterone System 2000 1: S10-S13.
Newcombe, C.P. et al, Sympathectomy for Hypertension, British Medical Journal, Jan. 1959, 142-144.
Ng, Fu Siong et al, Catheter Ablation of Atrial Fibrillation, Clinical Cardiology, 25, 384-394 (2002).
Norman, Roger A. et al, Role of the Renal Nerves in One-Kidney, One Clip Hypertension in Rats, Hypertension Journal of the American Heart Association, 1984;6:622-626.
Nozawa, Takashi et al, Effects of Long-Term Renal Sympathetic Denervation on Heart Failure After Myocardial Infarction in Rats, Heart Vessels (2002) 16:51-56.
O'Connor, Brian K. et al, Radiofrequency Ablation of a Posteroseptal Accessory Pathway Via the Middle Cardiac Vein in a Six-Year-Old Child, PACE, vol. 20, Oct. 1997, Part 1, 2504-2507.
O'Hagen, Kathleen P. et al, Renal Denervation Decreases Blood Pressure in DOCA-Treated Miniature Swine With Established Hypertension, American Journal of Hypertension, 1990; 3:62-64.
Oliveira, Vera L.L. et al, Renal Denervation Normalizes Pressure and Baroreceptor Reflex in High Renin Hypertension in Conscious Rats, Hypertension vol. 19, No. 2 Feb. 1992, Supplement II, II-17-II-21.
Omran, Heyder et al, Echocardiographic Imaging of Coronary Sinus Diverticula and Middle Cardiac Veins in Patients with Preexcitation Syndrome: Impact—on Radiofrequency Catheter Ablation of Posteroseptal Accessory Pathways, PACE, vol. 18, Jun. 1995, 1236-1243.
Oparil, Suzanne et al, Renal Nerve Ablation: Emerging Role in Therapeutics; Blood Pressure, Oct. 2011, vol. 20, No. 5, pp. 253-255.
Oral, Hakan et al, Pulmonary Vein Isolation for Paroxysmal and Persistent Atrial Fibrillation, Circulation Journal of The American Heart Association, 2002;105:1077-1081.
Osborn, Jeffrey L. et al, Long-Term Increases in Renal Sympathetic Nerve Activity and Hypertension, Clinical and Experimental Pharmacology and Physiology (1997) 24,72-76.
Osborn, John W., The Sympathetic Nervous System and Long-Term Regulation of Arterial Pressure: What Are the Critical Questions?, Clinical and Experimental Pharmacology and Physiology (1997) 24, 68-71.
Ou, Baiqing et al, Baroreflex Sensitivity Predicts the Induction of Ventricular Arrhythmias by Cesium Chloride in Rabbits, Japanese Circulation Journal, 1999; 63: 783-788.
Oz, Mehmet, Pressure Relief, TIME Magazine, Monday, Jan. 9, 2012.
Page, Irvine H. et al, Mechanisms, Diagnosis and Treatment of Hypertension of Renal Vascular Origin, Annal of Internal Medicine, Aug. 1959, vol. 51, No. 2, 196-211.
Page, Irvine H. et al, Mechanisms, Diagnosis and Treatment of Hypertension of Renal Vascular Origin; Annals of Internal Medicine, Aug. 1959;51:196-211.
Page, Irvine H. et al, The Effect of Renal Denervation on the Level of Arterial Blood Pressure and Renal Function in Essential Hypertension, Journal of Clinical Investigation, 1935;14(1):27-30.
Page, Irvine H. et al, The Effects of Renal Denervation on Patients Suffering from Nephritis, J Clin Invest. 1935;14 (4):443-458.
Page, Irvine H., The Effect of Renal Efficiency of Lowering Arterial Blood Pressure in Cases of Essential Hypertension and Nephritis, Journal of Clinical Investigation, Nov. 1934; 13(6): 909-915.
Page, Max, Section of Surgery, Discussion on the Surgical Treatment of Hypertension, Proceedings of the Royal Society of Medicine, vol. XLI, Feb. 1948, 359-372.

(56) References Cited

OTHER PUBLICATIONS

Papademetriou, Vasilios, Hypertension and the Simplicity Renal Denervation System, Scientific Background, www.medtronic.com, 2011.
Pappone, Carlo et al, Circumferential Radiofrequency Ablation of Pulmonary Vein Ostia: A New Anatomic Approach for Curing Atrial Fibrillation, Circulation, Journal of the American Heart Association, 2000;102:2619-2628.
Parati, Gianfranco et al, The Human Sympathetic Nervous System: Its Relevance in Hypertension and Heart Failure, European Heart Journal (2012) 33, 1058-1066.
Parmar, Arundhati, Analyst: Medtronic Will Likely Acquire Another Hypertension Therapy Firm, Medcity News, Apr. 27, 2012; 3:06 p.m.; medcitynews.com.
Pavlovich, Christian P. et al, Percutaneous Radio Requency Ablation of Small Renal Tumors: Initial Results; The Journal of Urology, vol. 167, Jan. 10-15, 2002.
Pearce, John A. et al, Blood Vessel Architectural Features and Their Effect on Thermal Phenomena, Critical Reviews, vol. CR75, Bellingham, WA: SPIE Optical Engineering Press; 2000, p. 231-277.
Peet, Max Minor, Hypertension and Its Surgical Treatment by Bilateral Supradiaphragmatic Splanchnicectomy, American Journal of Surgery, vol. 75, Issue 1, Jan. 1948, 48-68.
Perry, C. Bruce, Malignant Hypertension Cured by Unilateral Nephrectomy, British Heart Journal, Jul. 1945; 7(3): 139-142.
Persu, Alexandre et al, Renal Denervation: Ultima Ratio or Standard in Treatment-Resistant Hypertension, Hypertension Journal of The American Heart Association, Sep. 2012;60(3):596-606.
Peterson, Helen Hogh et al, Lesion Dimensions During Temperature-Controlled Radiofrequency Catheter Ablation of Left Ventricular Porcine Myocardium Impact of Ablation Site, Electrode Size, and Convective Cooling, Circulation Journal of The American Heart Association, 1999;99:319-325.
Plouin, Pierre-Francois et al, Blood Pressure Outcome of Angioplasty in Atherosclerotic Renal Artery Stenosis A Randomized Trial, Hypertension Journal of The American Heart Association, 1998;31:823-829.
Poutasse, Eugene F., Surgical Treatment of Renal Hypertension, American Journal of Surgery, vol. 107, Jan. 1964, 97-103.
Pugsley, M.K. et al, The Vascular System an Overview of Structure and Function, Journal of Pharmacological and Toxicological Methods 44 (2000) 333-340.
Putney, John Paul, Are Secondary Considerations Still "Secondary"?: An Examination of Objective Indicia of Nonobviousness Five Years After KSR, Intellectual Property Brief, vol. 4, Issue 2, Article 5, 2012, 45-59.
Ramsay, Lawrence E. et al, Blood Pressure Response to Percutaneous Transluminal Angioplasty for Renovascular Hypertension: An Overview of Published Series; British Medical Journal Mar. 3, 1990; 300(6724): 569-572.
Rippy, Marian K. et al, Catheter-Based Renal Sympathetic Denervation: Chronic Preclinical Evidence for Renal Artery Safety, Clin Res Cardiol (2011) 100:1095-1101.
Ritz, Eberhard, New Approaches to Pathogenesis and Management of Hypertension, Clin J Am Soc Nephrol 4: 1886-1891, 2009.
Jaff, Michael R. et al, Kidney Stenting Lowers Blood Pressure in Patients with Severe Hypertension; Catheterization and Cardiovascular Interventions; Published Online: Jun. 27, 2012 (DOI: 10.1002/ccd24449); Print Issue Date: Sep. 2012. URL: http://onlinelibrary.wiley.com/doi/10.1002/ccd.24449/abstract.
Jain, Mudit K. et al, A Three-Dimensional Finite Element Model of Radiofrequency Ablation with Blood Flow and Its Experimental Validation, Annals of Biomedical Engineering, vol. 28, pp. 1075-1084, 2000.
Jais, Pierre et al, Efficacy and Safety of Septal and Left-Atrial Linear Ablation for Atrial Fibrillation, The American Journal of Cardiology, vol. 84 (9A), Nov. 1999, 139R-146R.
Janssen, Ben J.A. et al, Frequency-Dependent Modulation of Renal Blood Flow by Renal Nerve Activity in Conscious Rabbits, American Journal of Physiology, 1997, 273:R597-R608.
Janssen, Ben J.A. et al, Renal Nerves in Hypertension, Miner Electrolyte Metab 1989;15:74-82.
Jin, Yu et al, No Support for Renal Denervation in a Meta-Analysis, JACC vol. 62, No. 21, 2013 Correspondence Nov. 19/26, 2013:2029-30.
Kaltenbach, Benjamin et al, Renal Artery Stenosis After Renal Sympathetic Denervation, J Am Coll Cardiol. Dec. 25, 2012;60(25):2694-5.
Kaltenbach, Benjamin et al, Renal Sympathetic Denervation as Second-Line Therapy in Mild Resistant Hypertension: A Pilot Study, Catheterization and Cardiovascular Interventions 81:335-339 (2013).
Kamiya, Atsunori et al, Parallel Resetting of Arterial Baroreflex Control of Renal and Cardiac Sympathetic Nerve Activities During Upright Tilt in Rabbits, Am J Physiol Heart Circ Physiol 298: H1966-H1975, 2010.
Kandzari, David E. et al, Catheter-Based Renal Denervation for Resistant Hypertension: Rationale and Design of the SYMPLICITY HTN-3 Trial, Clin. Cardiol. 35, 9, 528-535 (2012).
Kapural, Leonardo et al, Radiofrequency Ablation for Chronic Pain Control, Current Pain and Headache Reports 2001, 5:517-525.
Kassab, Salah et al, Renal Denervation Attenuates the Sodium Retention and Hypertension Associated with Obesity, Hypertension vol. 25, No. 4, Part 2 Apr. 1995.
Katholi, Richard E. et al, Decrease in Peripheral Sympathetic Nervous System Activity following Renal Denervation or Unclipping in the One-Kidney One-Clip Goldblatt Hypertensive Rat, The Journal of Clinical Investigation, Jan. 1982;69(1):55-62.
Katholi, Richard E. et al, Role of the Renal Nerves in the Pathogenesis of One-Kidney Renal Hypertension in the Rat, Hypertension. 1981;3:404-409.
Katholi, Richard E. et al, The Role of Renal Sympathetic Nerves in Hypertension: Has Percutaneous Renal Denervation Refocused Attention on Their Clinical Significance?; Progress in Cardiovascular Disease 52 (2009) 243-248.
Katritsis, Demosthenes et al, Recurrence of Left Atrium-Pulmonary Vein Conduction Following Successful Disconnection in Asymptomatic Patients, Europace (2004) 6, 425e432.
Killip III, Thomas, Oscillation of Blood Flow and Vascular Resistance During Mayer Waves, Circulation Research, vol. XI, Dec. 1962, 987-993.
Kingwell, Bronwyn A. et al, Assessment of Gain of Tachycardia and Bradycardia Responses of Cardiac Baroreflex, Am J Physiol Heart Circ Physiol 260:H1254-H1263, 1991.
Kirchheim, H. et al, Sympathetic Modulation of Renal Hemodynamics, Renin Release and Sodium Excretion, Klin Wochenschr (1989) 67: 858-864.
Klein, Ge et al, Endovascular Treatment of Renal Artery Aneurysms with Conventional Non-Detachable Microcoils and Guglielmi Detachable Coils, Br J Urol. Jun. 1997; 79(6):852-860.
Knight, Eric L. et al, Predictors of Decreased Renal Function in Patients with Heart Failure During Angiotensin-Converting Enzyme Inhibitor Therapy: Results from the Studies of Left Ventricular Dysfunction (SOLVD), American Heart Journal, vol. 138, No. 5, Part 1, Nov. 1999, 849-855.
Koepke, John P. et al, Functions of the Renal Nerves, The Physiologist, vol. 28, No. 1, Feb. 1985, 47-52.
Kompanowska-Jezierska, Elzbieta et al, Early Effects of Renal Denervation in the Anaesthetised Rat: Natriuresis and Increased Cortical Blood Flow, Journal of Physiology (2001), 531.2, pp. 527-534.
Krum, Henry et al, Catheter-Based Renal Sympathetic Denervation for Resistant Hypertension: A Multicentre Safety and Proof-of-Principle Cohort Study, www.thelancet.com vol. 373 Apr. 11, 2009 1275-1281.
Krum, Henry et al, Device-Based Antihypertensive Therapy: Therapeutic Modulation of the Autonomic Nervous System, Circulation. 2011;123:209-215.
La Grange, Ronald G. et al, Selective Stimulation of Renal Nerves in the Anesthetized Dog: Effect on Renin Release During Controlled Changes in Renal Hemodynamics, Circulation Research, Journal of The American Heart Association, 1973;33:704-712.
Labeit, Alexander Michael et al, Changes in the Prevalence, Treatment and Control of Hypertension in Germany? A Clinical-Epide-

(56) References Cited

OTHER PUBLICATIONS miological Study of 50.000 Primary Care Patients, PLOS ONE, Dec. 2012, vol. 7, Issue 12, e52229, 1-11.

Labonte, Sylvain, Numerical Model for Radio-Frequency Ablation of the Endocardium and its Experimental Validation, IEEE Transactions on Biomedical Engineering, vol. 41, No. 2. Feb. 1994, 108-115.

Lambert, Gavin W. et al, Health-Related Quality of Life After Renal Denervation in Patients With Treatment-Resistant Hypertension, Hypertension. 2012;60:1479-1484.

Lee, Sang Joon et al, Ultrasonic Energy in Endoscopic Surgery, Yonsei Medical Journal, vol. 40, No. 6, pp. 545-549, 1999.

Leertouwer, Trude C. et al, In-Vitro Validation, with Histology, of Intravascular Ultrasound in Renal Arteries, Journal of Hypertension 1999, vol. 17 No. 2, 271-277.

Leishman, A.W.D., Hypertension—Treated and Untreated, British Medical Journal, May 1959, 1361-1368.

Leonard, Bridget L. et al, Differential Regulation of the Oscillations in Sympathetic Nerve Activity and Renal Blood Flow Following Volume Expansion, Autonomic Neuroscience: Basic and Clinical 83 (2000) 19-28.

Levin, Stephen, Ardian: Succeeding Where Drugs Fail Treating Hypertension in the Cath Lab, In Vivo: The Business & Medicine Report, vol. 27, No. 10, Nov. 2009.

Litynski, Grzegorz S., Kurt Semm and the Fight against Skepticism: Endoscopic Hemostasis, Laparoscopic Appendectomy, and Semm's Impact on the "Laparoscopic Revolution", JSLS. Jul.-Sep. 1998; 2(3): 309-313.

Lu, David S.K. et al, Effect of Vessel Size on Creation of Hepatic Radiofrequency Lesions in Pigs: Assessment of the "Heat Sink" Effect, American Journal of Radiology, 178, Jan. 2002, 47-51.

Luscher, Thomas F. et al, Renal Nerve Ablation After SYMPLICITY HTN-3: Confused at the Higher Level?; European Heart Journal, doi:10.1093/eurheartj/ehu195; May 14, 2014.

Lustgarten, Daniel L. et al, Cryothermal Ablation: Mechanism of Tissue Injury and Current Experience in the Treatment of Tachyarrhythmias, Progress in Cardiovascular Diseases, vol. 41, No. 6 May/Jun. 1999: pp. 481-498.

Mahfoud, Felix et al, Expert Consensus Document from the European Society of Cardiology on Catheter-Based Renal Denervation, European Heart Journal, Jul. 2013;34(28):2149-57.

Mancia, Giuseppe et al, Sympathetic Activation in the Pathogenesis of Hypertension and Progression of Organ Damage, Hypertension Journal of the American Heart Association, 1999, 34:724-728.

Mcgahan, John P. et al, History of Ablation, Tumor Ablation, 2005, pp. 3-16.

Medtronic, Inc., J.P. Morgan Healthcare Conference, Corrected Transcript, Jan. 13, 2014, Factset:Callstreet, www.callstreet.com,.

Medtronic, Inc., Medtronic Announces U.S. Renal Denervation Pivotal Trial Fails to Meet Primary Efficacy Endpoint While Meeting Primary Safety Endpoint, www.medtronic.com, Jan. 9, 2014.

Medtronic, Inc., RDN Therapy with the Symplicity Renal Denervation System, Procedure Fact Sheet, www.medtronic.com, 2011.

Medtronic, Inc., Renal Denervation (RDN) Novel Catheter -based Treatment for Hypertension, Symplicity RDN System Common Q&A, 2011.

Medtronic, Inc., Scientific Basis Behind Renal Denervation for the Control of Hypertension, Dec. 2012, http://www.icimeeting.com/2012/images/stories/PDF/1448_Wilcox_I_Mon.pdf.

Mehdirad, Ali et al, Temperature Controlled RF Ablation in Canine Ventricle and Coronary Sinus using 7 Fr or 5 Fr Ablation Electrodes, PACE, vol. 21, Jan. 1998, Part II, 316-321.

Meredith, I T et al, Exercise Training Lowers Resting Renal But Not Cardiac Sympathetic Activity in Humans; Hypertension Journal of The American Heart Association, 1991;18:575-582.

Michaelis, Lawrence L. et al, Effects of Renal Denervation and Renin Depletion on the Renal Responses to Intravascular Volume Expansion, Ann Surg. Mar. 1972; 175(3): 424-430.

Millard, F.C. et al, Renal Embolization for Ablation of Function in Renal Failure and Hypertension, Postgraduate Medical Journal (1989) 65,729-734.

Zazgornik, Jan et al, Bilateral Nephrectomy: The Best, but Often Overlooked, Treatment for Refractory Hypertension in Hemodialysis Patients, AJH 1998; 11:1364-1370.

* cited by examiner

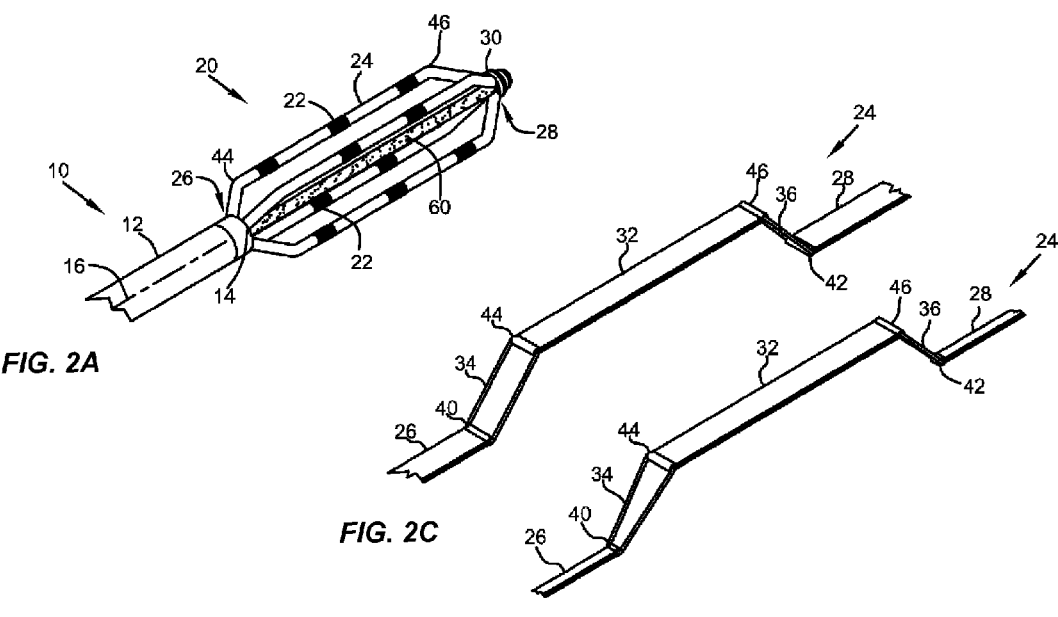
*FIG. 2A*
*FIG. 2C*
*FIG. 2D*
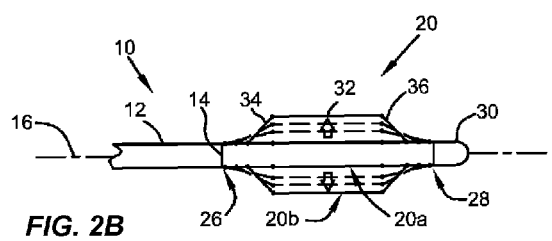
*FIG. 2B*

_MEDIGUIDE-ENABLED RENAL DENERVATION SYSTEM FOR ENSURING WALL CONTACT AND MAPPING LESION LOCATIONS_

BACKGROUND OF THE INVENTION

The present invention is related to ablation devices, and more particularly to devices, systems, and methods for mediguide-enabled renal denervation.

Hypertension is a major global public health concern. An estimated 30-40% of the adult population in the developed world suffers from this condition. Furthermore, its prevalence is expected to increase, especially in developing countries. Diagnosis and treatment of hypertension remain suboptimal, even in developed countries. Despite the availability of numerous safe and effective pharmacological therapies, including fixed-drug combinations, the percentage of patients achieving adequate blood-pressure control to guideline target values remains low. Thus, the development of new approaches for the management of hypertension is a priority. These considerations are especially relevant to patients with so-called resistant hypertension (i.e., those unable to achieve target blood-pressure values despite multiple drug therapies at the highest tolerated dose). Such patients are at high risk of major cardiovascular events.

Renal sympathetic efferent and afferent nerves, which lie within and immediately adjacent to the wall of the renal artery, are crucial for initiation and maintenance of systemic hypertension. Indeed, sympathetic nerve modulation as a therapeutic strategy in hypertension had been considered long before the advent of modern pharmacological therapies. Radical surgical methods for thoracic, abdominal, or pelvic sympathetic denervation has been successful in lowering blood pressure in patients with so-called malignant hypertension. However, these methods were associated with high perioperative morbidity and mortality and long-term complications, including bowel, bladder, and erectile dysfunction, in addition to severe postural hypotension. Renal denervation is the application of a chemical agent, or a surgical procedure, or the application of energy to partially or completely damage renal nerves so as to partially or completely block renal nerve activity. Renal denervation reduces or completely blocks renal sympathetic nerve activity, increases renal blood flow (RBF), and decreases renal plasma norepinephrine (NE) content.

The objective of renal denervation is to neutralize the effect of the renal sympathetic system, which is involved in arterial hypertension. One method to reach this objective is to use radio frequency (RF) ablation of renal sympathetic nerves to reduce the blood pressure of certain patients. There is a need for devices and techniques that are designed to improve the effectiveness of the procedure.

BRIEF SUMMARY OF THE INVENTION

To achieve these goals, a system and method that include a mediguide-enabled ablation catheter and specific techniques of overcoming these challenges are proposed.

In some embodiments, an ablation catheter includes an elongated body having a proximal end and a distal end, at least one ablation element disposed on the body between the proximal end and the distal end, and at least one localization sensor disposed on the body and configured to interact with a magnetic field.

In some embodiments, an ablation catheter includes a longitudinal rod, a plurality of arms disposed about the longitudinal rod, and being resiliently biased outwardly away from the longitudinal rod, at least one ablation element disposed on each of the arms, and at least one localization sensor disposed on at least one of the longitudinal rod and one of the plurality of arms.

In some embodiments, a method for ablating vascular tissue includes introducing into an artery an ablation catheter including an elongated body having a proximal end and a distal end, at least one ablation element disposed on the body between the proximal end and the distal end, and at least one localization sensor disposed on the body, using the at least one localization sensor to determine an appropriate target tissue for ablation and ablating the target tissue to provide a therapeutic effect.

BRIEF DESCRIPTION OF THE DRAWINGS

Various embodiments of the present system and method will now be discussed with reference to the appended drawings. It is to be appreciated that these drawings depict only some embodiments and are therefore not to be considered as limiting the scope of the present system and method.

FIGS. 2A-D illustrate an assembly of staggered ablation elements for a catheter;

DETAILED DESCRIPTION

In the description that follows, the terms "proximal" and "distal" are to be taken as relative to a user (e.g., a surgeon or a physician) of the disclosed devices and methods. Accordingly, "proximal" is to be understood as relatively close to the user, and "distal" is to be understood as relatively farther away from the user.

Figure 1:
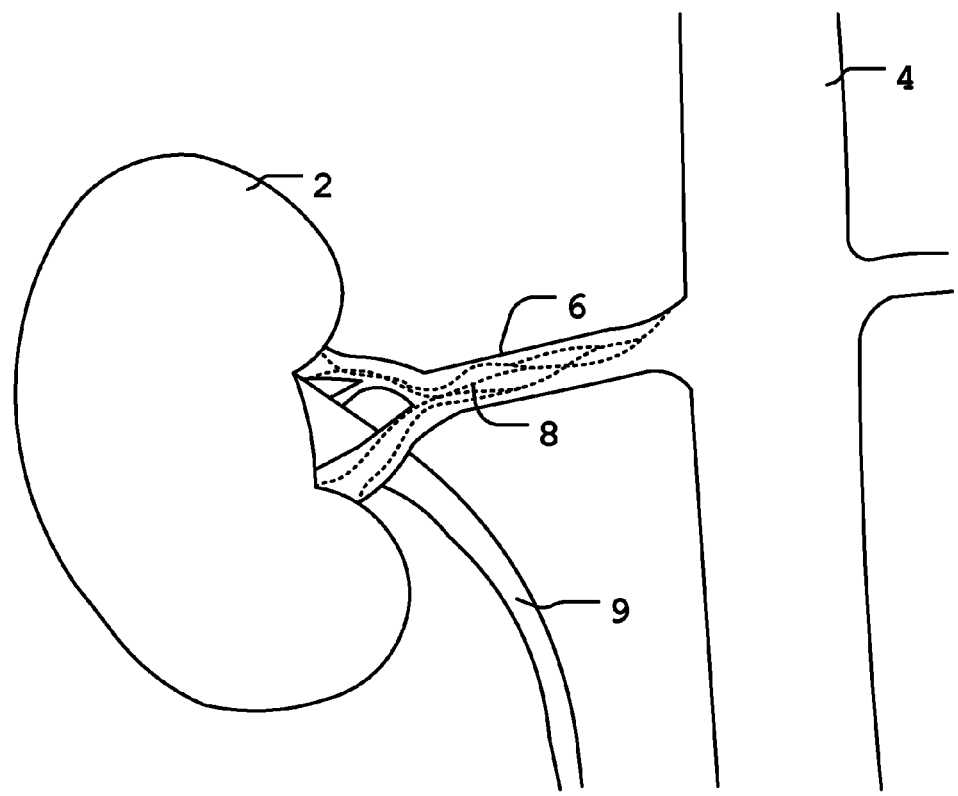
FIG. 1 is a schematic illustration of a kidney, the renal artery and the aorta.

FIG. 1 is a schematic representation of a kidney and its associated structures. The human body typically includes two kidneys 2, one on each side of the vertebral column. The kidneys serve to filter waste products from the blood. After filtration, urine passes from each bean-shaped kidney 2 via ureter 9 to the bladder (not shown). As seen in FIG. 1, kidneys 2 receive blood from aorta 4 through renal artery 6. Though the main function of the kidneys 2 is to remove waste products from the body, they also play a role as a regulatory organ. Specifically, it has been determined that renal sympathetic efferent and afferent nerves 8, which lie within and adjacent to the wall of the renal artery 6, play a role in managing blood pressure. Elevated renal nerve activity is associated with the development of hypertension.

FIGS. 2A-D illustrate an assembly of staggered ablation elements for an ablation catheter. In the perspective view of FIG. 2A, an ablation catheter 10 includes an elongated catheter body 12 extending between a proximal end (not shown) and a distal end 14 along a longitudinal axis 16 of the body. An ablation element assembly 20 includes a plurality of ablation elements 22 connected to the catheter body 12. The ablation elements 22 are discretely spaced from one another longitudinally and/or laterally. At least two of the ablation elements 22 may be spaced from one another longitudinally.

In this embodiment, the ablation elements 22 are electrodes, such as RF electrodes. The ablation element assembly 20 is connected to the distal end 14 of the catheter body 12. As seen in FIGS. 2A-D, the electrode assembly 20 includes a plurality of arms 24, each of which may be oriented generally parallel to the longitudinal axis 16. Each arm 24 has a proximal end 26 connected to the catheter body 12 and a distal end 28. The distal ends 28 of the arms 24 are connected at a distal junction 30. Each arm 24 includes an intermediate segment 32, a proximal stiffness change between the proximal end 26 and the intermediate segment, and a distal stiffness change between the distal end 28 and the intermediate segment. The arms 24 include a plurality of ablation electrodes 22 on the intermediate segments 32. A longitudinal rod 60 extends along the longitudinal axis 16. The distal end 28 of arm 24 may be coupled to longitudinal rod 60 while the proximal end 26 is coupled to distal end 14 of catheter body 12.

As shown in FIG. 2B, because of the attachment of arms 24 to rod 60 at one end and body 12 at the other end, the electrode assembly 20 is movable between a collapsed condition 20*a* and an expanded condition 20*b*, with the intermediate segments 32 of the arms 24 in the expanded condition moving outwardly relative to the proximal ends 26 and distal ends 28 of the arms in the collapsed condition.

Each arm 24 includes a proximal leg 34 coupled between the intermediate segment 32 and the proximal end 26 of the arm, and a distal leg 36 coupled between the intermediate segment and the distal end 28 of the arm. Each arm 24 also includes a proximal hinge 44 coupled between the proximal leg 34 and the intermediate segment 32 and a distal hinge 46 coupled between the distal leg 36 and the intermediate segment. The hinges 44, 46 represent the stiffness changes in this embodiment to facilitate movement of the intermediate segments 32 of the arms 24 between the collapsed condition 20*a* and the expanded condition 20*b*. In addition, each arm 24 may further include a proximal end hinge 40 coupled between the proximal leg 34 and the proximal end 26 and a distal end hinge 42 coupled between the distal leg 36 and the distal end 28 to further facilitate movement of the intermediate segments 32 of the arms between the collapsed condition 20*a* and the expanded condition 20*b*.

In use, the catheter 10 with the electrode assembly 20 is inserted into a blood vessel or the like in the collapsed condition 20*a* (inside a guiding sheath or the like) and deployed into the expanded condition 20*b*. To allow blood to flow past the electrode assembly 20 in the blood vessel and reduce or avoid obstruction, the arm 24 in FIG. 2C has a narrow intermediate segment 32, proximal leg 34, and distal leg 36. In FIG. 2D, the intermediate segment 32 is wider while the proximal leg 34 and distal leg 36 are tapered so as to be smaller in cross-section than the intermediate segment, thereby reducing obstruction. Furthermore, the electrode assembly 20 preferably has no sharp corners or edges, but has rounded corners and edges to facilitate easier and smoother movement within the blood vessel. Proximal leg 34 and distal leg 36 may also be hollow to allow blood to flow therethrough.

The ablation electrodes 22 in the expanded condition 20*b* contact the tissue and denervate nerves by raising the temperature and burning some of the nerves. To improve surface contact for the ablation electrodes 22, the intermediate segments 32 preferably have sufficient stiffness to avoid or minimize bending in the expanded condition 20*b*. The electrode assembly 20 may move from the collapsed condition 20*a* to the expanded condition 20*b* by any suitable mechanism. In one example, any or all of the proximal legs 34, the distal legs 36, the proximal end hinges 40, and the distal end hinges 42 of the arm 24 may be resiliently biased (e.g., with a spring or a memory material) to move the electrode assembly 20 toward the expanded condition 20*b*. In another example, a longitudinal rod 60 in the center of the electrode assembly 20 may be connected to the distal junction 30, and may be used to pull the distal junction 30 toward the distal end 14 of the catheter body 12 to move the electrode assembly 20 toward the expanded condition 20*b*.

Figure 3:
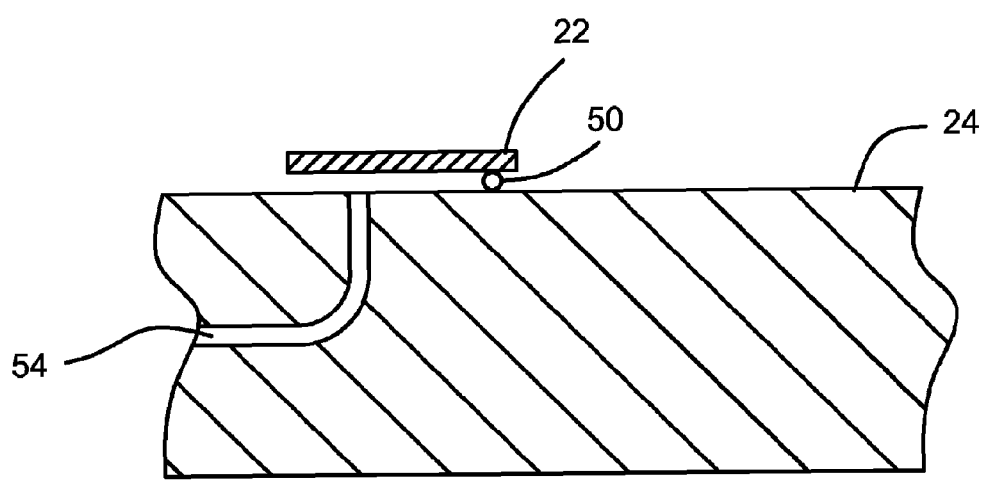
FIG. 3 is a cross-sectional view of an arm of an electrode assembly illustrating an example of a temperature sensor and an irrigation fluid channel.

A plurality of temperature sensors 50 may be thermally coupled with the plurality of ablation electrodes 22 to measure the temperatures of the ablation electrodes. FIG. 3 is a cross-sectional view of an arm 24 illustrating an example of a temperature sensor 50 disposed adjacent the electrode 22 supported on the arm. In addition, the arms 24 may include a plurality of irrigation fluid channels 54 near the plurality of ablation electrodes 22 to direct irrigation fluid toward the ablation electrodes 22, as seen in FIG. 3.

Figures 4A, 4B:
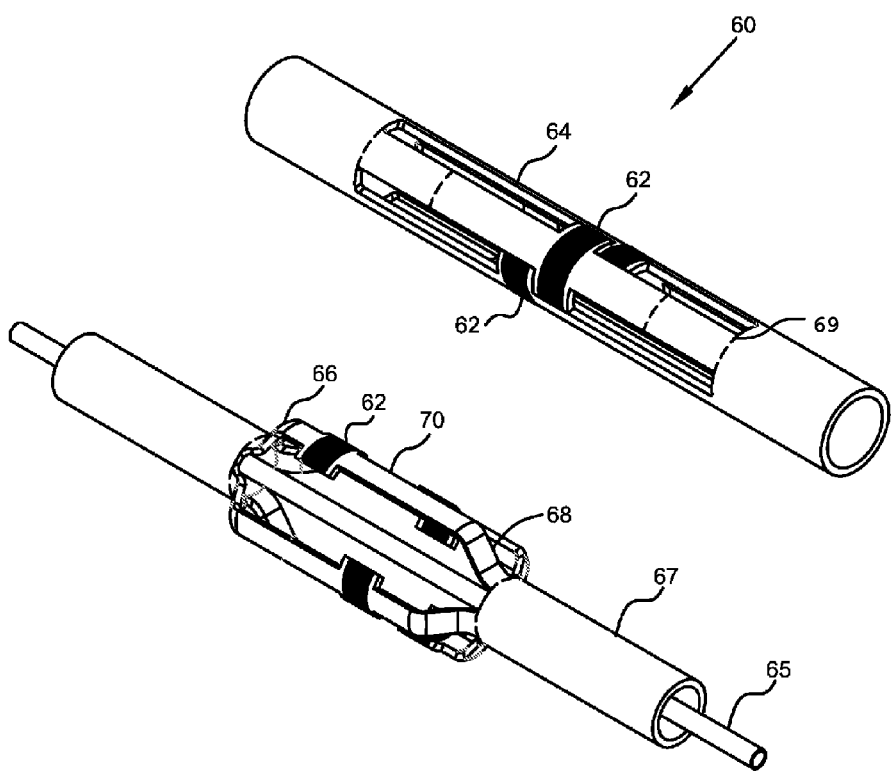
FIGS. 4A and 4B are perspective views of an assembly of staggered ablation elements for a catheter.

FIG. 4 illustrates an alternative configuration of a staggered ablation electrode assembly. FIG. 4A shows the electrode assembly 60 in a collapsed condition and FIG. 4B shows the electrode assembly 60 in an expanded configuration. The electrode assembly 60 may be connected to the distal end of a catheter body or may be disposed proximally from the distal end of the catheter body.

The electrode assembly 60 of FIG. 4 differs from the electrode assembly 20 of FIG. 2 in several respects. First, each ablation electrode 62 has a lateral dimension which is greater than its longitudinal dimension. The lateral dimension of the electrode 62 is greater than the lateral dimension of the arm 64 that supports the electrode. Each arm 64 has a proximal leg 66, a distal leg 68, and an intermediate segment 70. Each electrode 62 has the shape of a circumferential arch that produces an ablation zone that is oriented laterally with respect to the longitudinal axis. Such an ablation zone is more efficient and effective for ablating renal nerves that are oriented generally longitudinally.

Unlike the electrode assembly 20 of FIG. 2, the electrode assembly 60 of FIG. 4 does not include hinges on the arms.

Rather, the arms 64 are configured to facilitate movement of the electrode assembly 60 from the collapsed condition to the expanded condition. For example, the proximal leg 66 has a lower stiffness than the intermediate segment 70 and the distal leg 68 has a lower stiffness than the intermediate segment. The arms may further include weakened portions 69, showed by dashed lines, to aid in bending. A longitudinal rod 65 in the center of the electrode assembly 60 may be connected to the distal junction 67, and can be used to pull the distal junction 67 in the proximal direction to move the electrode assembly 60 toward the expanded condition. Distal legs 68 may be attached to distal junction 67, while proximal legs 66 remain affixed to inner rod 65. As a result, by moving distal junction 57 relative to rod 65, the proximal leg 66 and the distal leg 68 will bend or deform under a force that moves the electrode assembly 60 to the expanded condition. That force may be produced by forming at least one of the arms 64 of a shape memory material (e.g., nitinol).

Figures 5A, 5B:
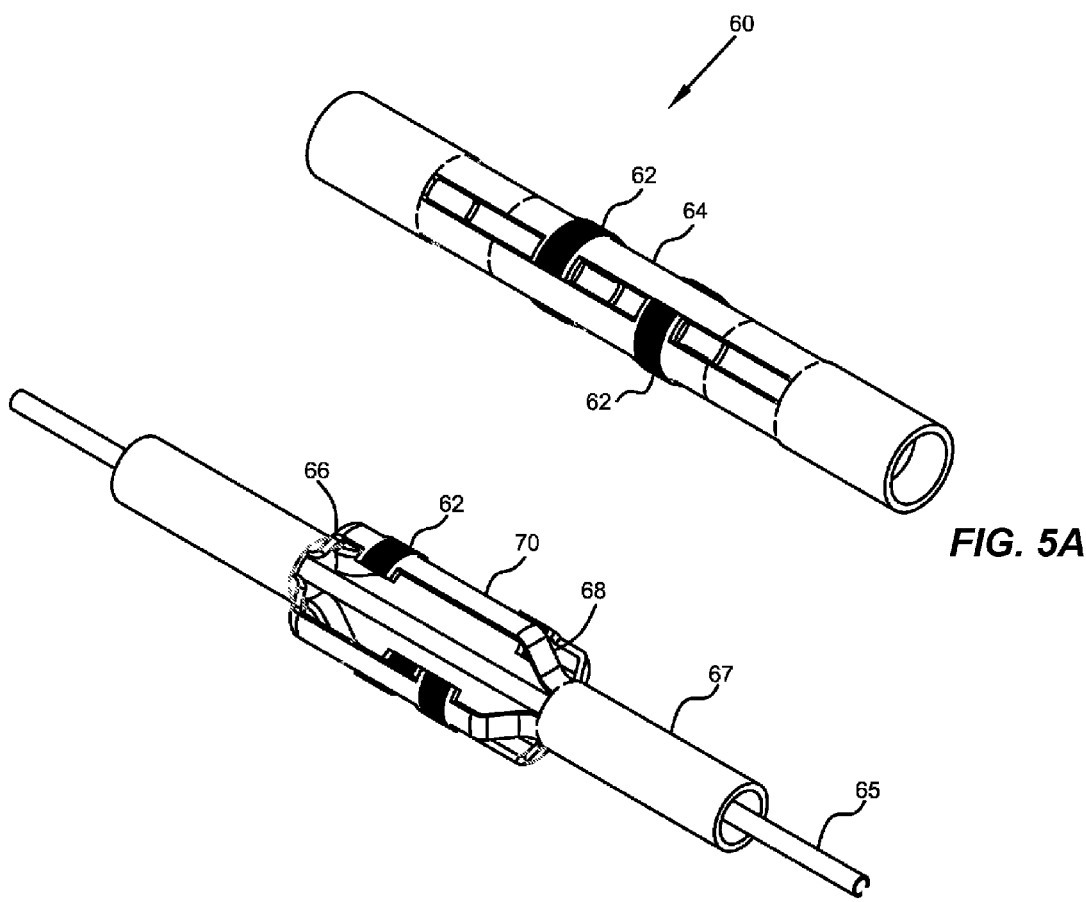
FIGS. 5A and 5B are perspective views of another electrode assembly of staggered ablation elements for a catheter.

The electrode assembly 60 of FIG. 5 is similar to the electrode assembly 60 of FIG. 4. They differ only in the arrangement of the ablation electrodes 62. In FIG. 4, the ablation electrodes 62 are staggered in a spiral manner in the longitudinal direction. In FIG. 5, the ablation electrodes 62 are arranged in nearly diametrically opposing pairs. These examples illustrate a few of the many different ways to arrange the staggered ablation electrodes 62 to form the electrode assemblies 60.

Figure 6:
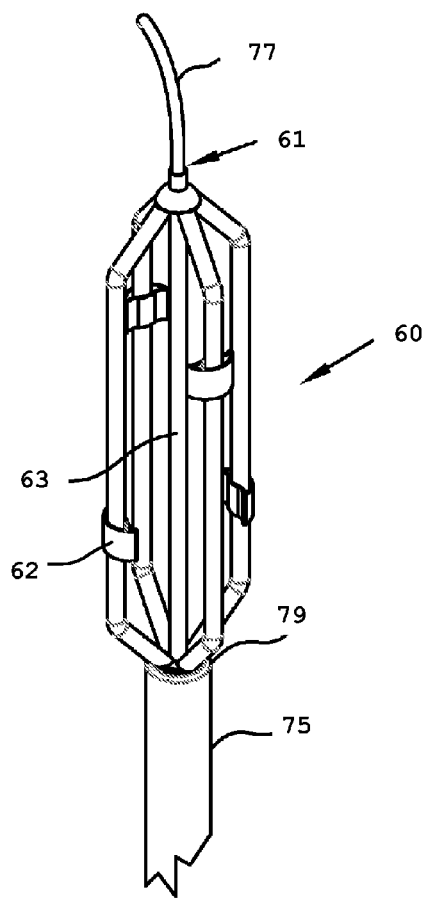
FIG. 6 is a perspective view of an over-the-wire configuration for introducing an assembly of staggered ablation elements on a catheter to the surgical site by passing a guide wire through an internal lumen of the catheter.
Figure 7:
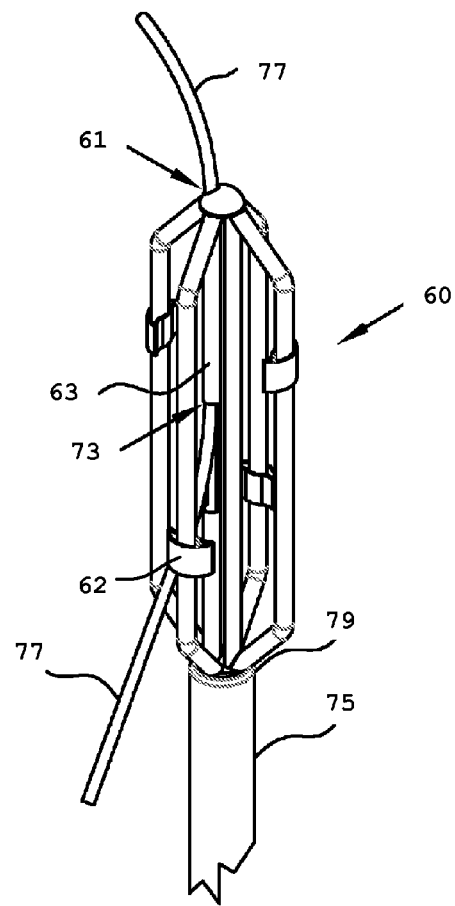
FIG. 7 is a perspective view of an over-the-wire configuration for introducing an assembly of staggered ablation elements on a catheter to the surgical site by passing a guide wire through a hole provided at the distal end of the assembly of staggered ablation elements.

Guide wires may be used to introduce the aforementioned ablation assemblies into the body. FIGS. 6 and 7 illustrate two methods of guiding the ablation assembly over the guide wire. FIG. 6 shows an over-the-wire configuration for introducing the assembly 60 of staggered ablation electrodes 62 on a catheter 75 to the surgical site by passing a guide wire 77 through an internal lumen of the catheter. The guide wire 77 extends through an opening 61 at the distal end of the electrode assembly 60, and through a tube 63 that extends through the assembly 60 to the internal lumen of catheter 75 from the catheter's distal end 79 to catheter's proximal end (not shown). The distal end of the assembly 60 is disposed distally of the distal end 79 of the catheter 75.

FIG. 7 illustrates an alternative over-the-wire configuration for introducing the assembly 60 of staggered ablation electrodes 62 on a catheter 75 to the surgical site. A guide wire 77 is passed through an opening 61 provided at the distal end of the assembly 60. The guide wire 77 then passes into a tube 63 and out therefrom through an intermediate opening 73 therein. Guidewire 77 then extends externally of the catheter 75 toward the proximal end of the catheter. In FIG. 7, both the distal opening 61 and the intermediate opening 73 are disposed distally of the distal end 79 of catheter 75.

As previously noted, ablation element localization may affect the efficacy of the treatment. To improve positioning, the electrode assembly 60 may include other structural components and materials, such as a magnetic material to enable sensing of the assembly through use with a magnetic location system, such as, for example, the guided Medical Positioning System ("gMPS") from MediGuide Ltd., and as generally shown in U.S. Pat. No. 7,386,339 entitled "Medical Imaging and Navigation System," the disclosure of which is incorporated herein by reference in its entirety.

The gMPS is intended to enable real time positioning and navigation of a gMPS-enabled diagnostic or therapeutic invasive device used in vascular or cardiac procedures. The gMPS consists of a miniaturized gMPS localization sensor, which is assembled on a device interacting with a magnetic field. When the gMPS sensor is located in a controlled low-intensity surrounding magnetic field, it provides real-time tip location and orientation data. The system may acquire a series of angiographic images and merge the position and orientation signals of the gMPS sensor with these images.

Figure 8A:
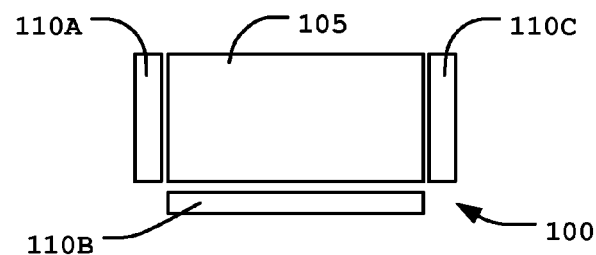
FIG. 8A is a schematic front view of a magnetic transmitter assembly.

A magnetic transmitter assembly (MTA) creates the requisite magnetic field. The MTA is installed on an x-ray detector, located at a distance of about 5 cm to about 30 cm above the relevant body part to be treated. The MTA's function is to generate a well-defined, changing magnetic field in a confined space, referred to as a motion box, above the target tissue. FIG. 8A is a schematic representation of a magnetic transmitter assembly 100, which is composed of three magnetic transmitter units (MTUs) 110A, 110B, 110C; two MTUs, 110A and 110C, are located on opposite sides of an x-ray detector 105 and one MTU, 110B, is located on the front of the x-ray detector.

Figure 8B:
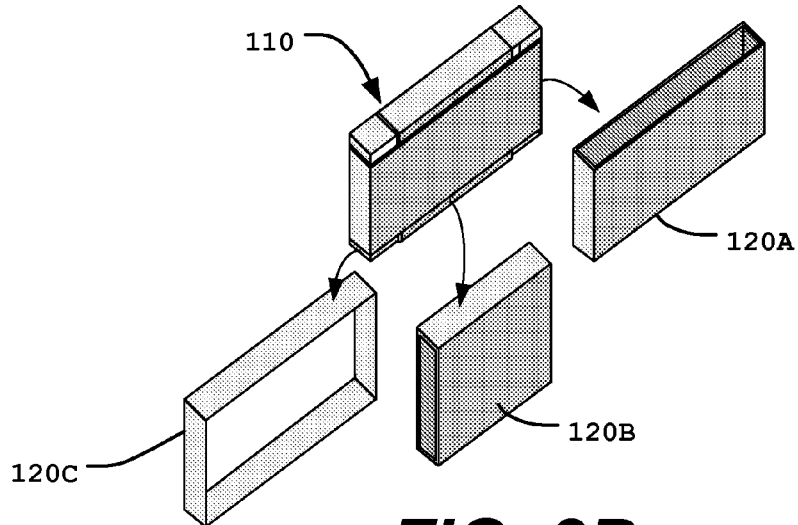
FIG. 8B is a schematic exploded view of three coils forming a magnetic transmitter unit.

As seen in FIG. 8B, each MTU 110 includes three separate orthogonal coils 120A, 120B, 120C that are assembled together. Because magnetic transmitter assembly 110 utilizes three MTUs, there are nine total orthogonal coils in the assembly. The magnetic transmitter assembly 100 generates AC magnetic and electrical fields, typically in the range of 9-15 KHz. These nine coils within the MTA are driven by nine concurrent power amplifiers from a controller (not shown). The controller also supplies nine loadable sine signals that drive the nine coils at practical frequencies that range from about 9 kHz to about 15 kHz. Thus, every coil is driven at a fixed frequency. Table 1 below is an example of nine frequencies applied at the nine coils:

TABLE 1

| | \multicolumn{9}{c}{Frequency table} |
|---|---|---|---|---|---|---|---|---|---|
| | \multicolumn{9}{c}{Channel} |
| | 1 | 2 | 3 | 4 | 5 | 6 | 7 | 8 | 9 |
| Frequency [kHz] | 11.125 | 12.375 | 9.875 | 11.625 | 12.875 | 10.25 | 12.125 | 13.25 | 10.75 |

Figure 8C:
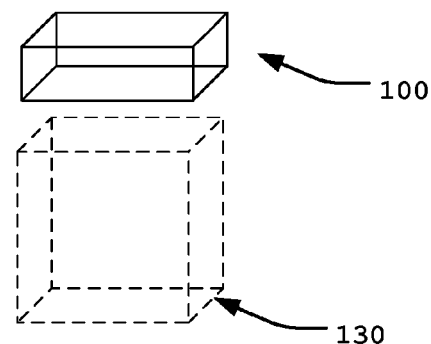
FIG. 8C is a schematic exploded view of a magnetic transmitter assembly and a corresponding motion box formed underneath the assembly.

Exciting the nine coils creates a magnetic field in a virtual 3D space under MTA 100 called the motion box 130, shown in FIG. 8C. During system operation for clinical use, a treatment device includes any number of gMPS sensors that detect the magnetic fields from the nine coils and thus provide data relating to location and orientation of the gMPS sensors (e.g., x, y, and z components, roll, pitch and yaw). Thus, when such a device having multiple gMPS sensors is placed within the motion box it can be tracked inside the vasculature.

Figure 9A:
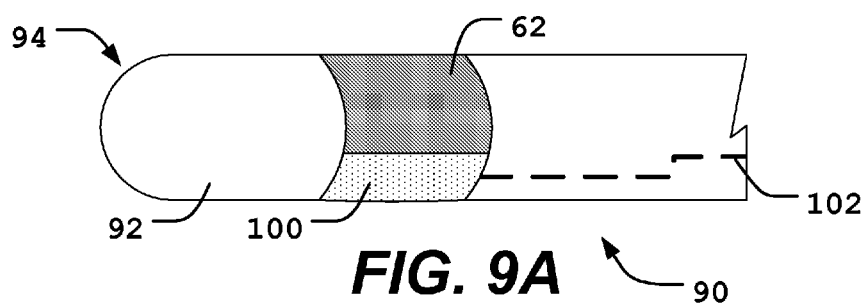
FIGS. 9A-C are various configurations of an electrode assembly having localization sensors according to one embodiment of the present invention.

An electrode assembly may be constructed to ablate tissue while using the magnetic location system described above for localization. In a simple configuration shown in FIG. 9A, an electrode assembly 90 includes a single tubular body 92 and a single ablation electrode 62 for ablating tissue in the renal artery. A single localization sensor 100 is located circumferentially adjacent ablation electrode 62 and connected via a wire 102 through body 92 to a processor (not shown). Each localization sensor may be formed of an electric conductor that winds to form a coil, or other shape to generate a stable signal. In one example, the localization sensor may be formed of a sub-millimeter copper wire. The localization sensor may include gMPS sensors or any other suitable sensor capable of determining a position, an orientation or both a position and an orientation of a medical device. In some examples, the localization sensor may be spaced away from an adjacent ablation electrode so as not to be in contact with the ablation electrode in order to avoid interference during ablation. Localization sensor 100 may be made of a radiopaque material or coated with such a material, thereby being detectable by an imaging device, such as radiographic, fluoroscopic, magnetic or sonographic devices. Localization sensor 100 detects an electromagnetic field from the MTUs and produces a respective electrical analog signal, which is then digitized and used to indicate the location and orientation of the sensor.

Figure 9B:
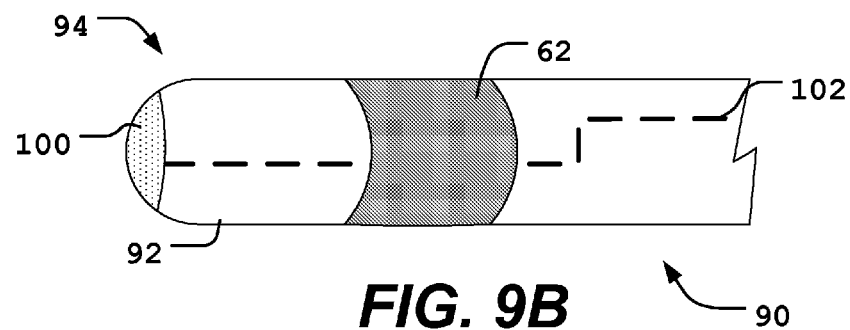

FIG. 9B illustrates a similar electrode assembly 90 but shows that the localization sensor 100 may be disposed at a distal end 94 of body 92 spaced from ablation electrode 62 rather than being located adjacent the ablation electrode. With the localization sensor 100 located at distal end 94, the position and orientation of the tip of the electrode assembly 90 may be identified within the renal artery. The location of localization sensor 100 may be varied and may depend on the type of sensor being used. For example, if localization sensor 100 is made of copper, it may be beneficial to isolate the sensor from blood flow, while keeping it as close to the surface of electrode assembly 90 as possible to maintain accurate localization.

Figure 9C:
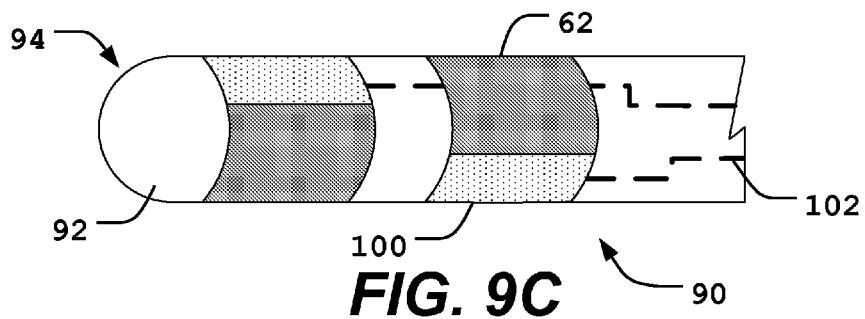

In another configuration, shown in FIG. 9C, multiple ablation electrodes 62 are disposed on body 92. Each ablation electrode 62 may be circumferentially adjacent to a designated localization sensor 100, which is connected to a wire 102. Thus, multiple localization sensors 100 may be disposed on body 92 to show the location of each ablation electrode 62.

Figure 9D:
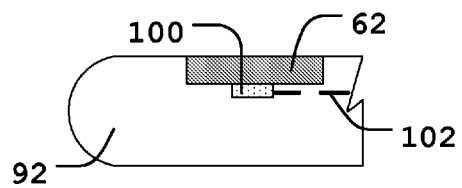
FIG. 9D is a schematic cross-sectional view of a localization sensor disposed under an ablation electrode according to one embodiment of the present invention.
Figure 9E:
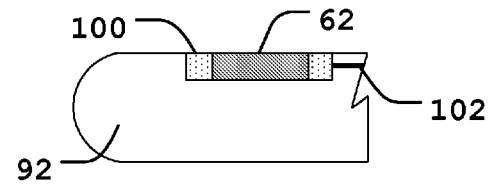
FIG. 9E is a schematic cross-sectional view of a localization sensor disposed around an ablation electrode according to another embodiment of the present invention.

It will be understood that while the preceding examples illustrate localization sensors 100 disposed on body 92 adjacent to or spaced from ablation electrodes 62, the localization sensors may be disposed under each ablation electrode and connected to a wire 102 disposed within the body (FIG. 9D). Alternatively, the localization sensors may be placed around each ablation electrode 62 (FIG. 9E).

Figure 10A:
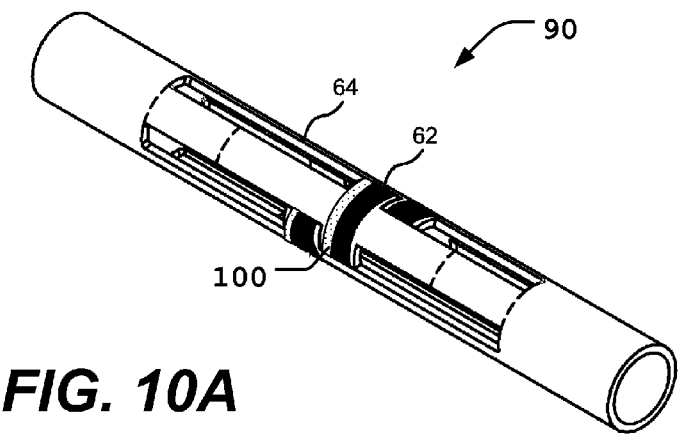
FIGS. 10A and 10B are perspective views of an assembly of staggered ablation elements for a catheter including a plurality of localization sensors according to another embodiment of the present invention.
Figure 10B:
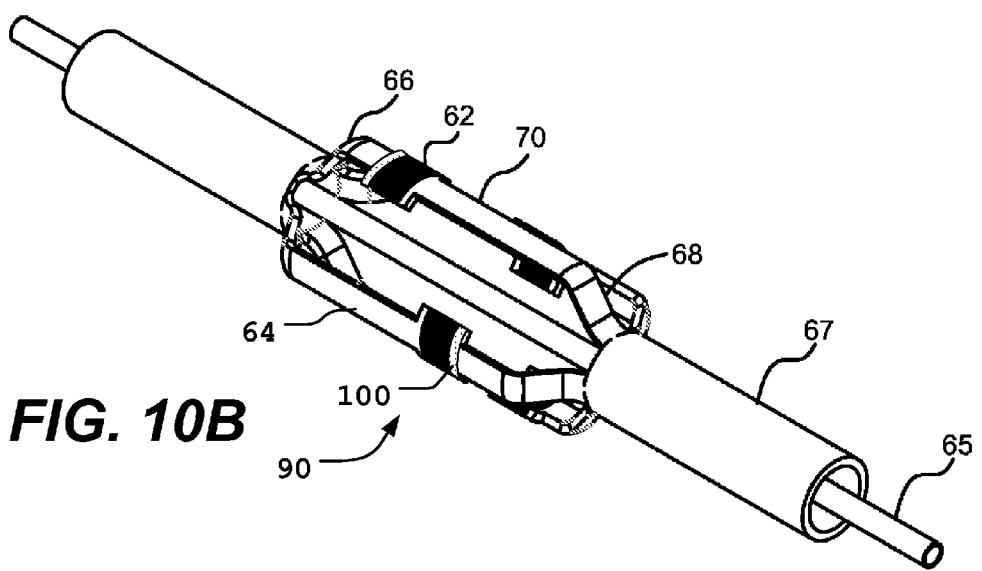

FIGS. 10A and 10B illustrate an electrode assembly 90 including a plurality of ablation electrodes 62 and localization sensors 100 disposed on the intermediate segment 70 of arms 64. In this specific example, electrode assembly 90 includes four arms 64 and a localization sensor 100 disposed on each arm 64 near each of the ablation electrodes 62. Though FIG. 10 illustrates localization sensors 100 disposed immediately adjacent each of the ablation electrodes 62, it will be understood that localization sensors 100 may be disposed on less than all of the arms 64, at any location near the arms (e.g., anywhere between proximal leg 66 and distal leg 68) or at the distal tip of the electrode assembly 90 as shown in FIG. 9B.

The localization sensors 100 provide a number of benefits. First, the localization sensors 100 may facilitate the location of lesion sites by providing three-dimensional sensor location at higher precision than with the two-dimensional projections of conventional fluoroscopy. Second, the localization sensors 100 may further provide the relative positions of additional lesions after moving the ablation catheter as the old and new catheter positions may be registered on the same image or three-dimensional model of the renal artery. Third, localization sensors 100 may facilitate contact between the ablation electrodes and the arterial wall. This is because a rotational angiogram of the renal artery may allow construction of a three-dimensional model of the arterial lumen, and a localization sensor's precise location is capable of indicating whether the ablation electrodes are in direct proximity to a vessel wall. Moreover, analysis of the sensors' motion characteristics, such as the position and orientation of the individual sensors, may distinguish between firm and inadequate contact with the arterial wall.

Figure 11:
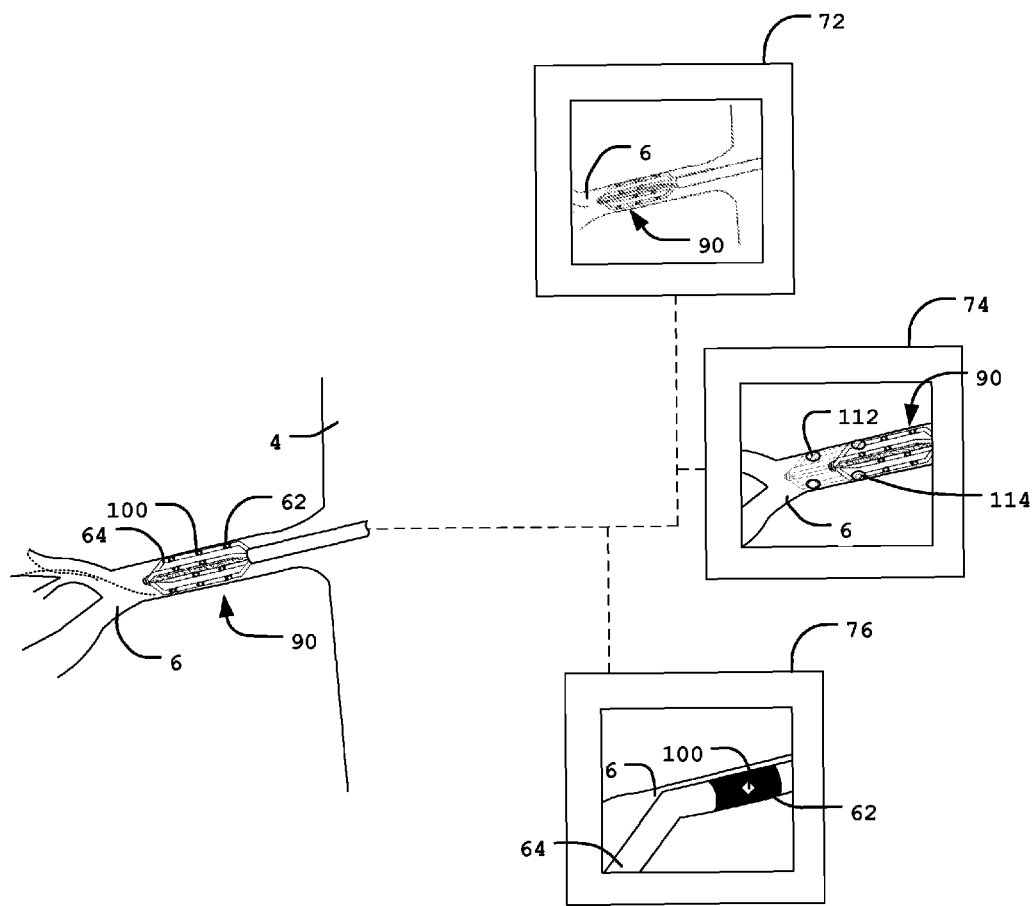
FIG. 11 diagrammatically illustrates real-time visual displays of the catheter location within the renal artery according to one embodiment of the present invention.

These principles are illustrated in more detail in FIG. 11. In this example, electrode assembly 90 is inserted into renal artery 6, the electrode assembly having a plurality of arms 64, each arm having an ablation electrode 62 and a localization sensor 100. The localization sensors 100 are coupled to multiple visual displays 72, 74, 76 to facilitate treatment.

For the sake of clarity, FIG. 11 illustrates three separate visual displays although it will be understood that a single visual display may display any of the techniques described below in multiple windows either at the same time or sequentially. Visual display 72 illustrates the position of the electrode assembly 90 within a three-dimensional angiogram model of the renal artery by utilizing localization sensors 100. Thus, the physician may obtain better visualization of the electrode assembly and more precisely locate same to form a lesion in the renal artery at a desired site.

Visual display 74 illustrates the technique of visualizing a first set of lesions 112 on the display and moving the electrode assembly 90 so that new lesions are formed at second positions. Specifically, the positions of old lesions 112 are registered using localization sensors 100 on the three-dimensional model and displayed using icons, colors, shading or the like, while the electrode assembly 90 is rotated and or translated within renal artery 6. A second set of lesions may then be formed in the renal artery while appreciating the positions of older lesions 112.

In one alternative, visual display 74 may register the positions of the first set of lesions 112 and display, using icons, colors or shading, preferred positions 114 for creating the second set of lesions. Thus, the physician may ablate tissue to create a first set of lesions and the localization sensors 100 may guide the placement of the second set. Specifically, after forming the first set of lesions 112, the localization sensors may register the locations of this first set. A visual icon may automatically inform the physician where to create the second set of lesions and the physician may simply move and rotate the electrode assembly 90 so that the ablation electrodes 62 align with the preferred positions 114 and ablate at those sites, thereby creating two sets of lesions that provide the best therapeutic result. The system may provide an alert, such a visual, auditory or tactile alert, to confirm that the ablation electrodes 62 are properly aligned with the preferred positions 114.

Visual display 76 may provide an enlarged view showing the position of an ablation electrode 62 with respect to the wall of renal artery 6. Initially, a rotational angiogram of renal artery 6 may allow generation of a three-dimensional model and the precise localization of a localization sensor 100 may indicate the proximity of ablation electrode 62 to the arterial wall through visual inspection. Using the three-dimensional model, the distance between the localization sensor 100 and the arterial wall may be seen by the physician on the visual display 76 and adequate wall contact may be determined. Additionally, a reconstruction feature such as the AngioSurvey 3D Reconstruction feature or similar may be used to create a three-dimensional model of coronary vessels that can be overlaid and merged with the live three-dimensional tracking of the localization sensor. One such feature for three-dimensional reconstruction is described in U.S. Pat. No. 7,840,252, which is incorporated herein by reference in its entirety. Using this technique or a similar one, the distance between the arterial wall and the localization sensors may be computed and adequate wall contact may be determined based on this computation.

In addition to visual inspection and distance analysis, through real-time analysis of the motion of localization sensors 100, proper contact with the arterial wall may be determined. The reason hypothesized for this phenomenon is that a localization sensor 100 will move less when it is in contact with the arterial wall. Specifically, sensors deployed but not fully in contact with the arterial wall will both translate and rotate cyclically as blood pressure pulses through the renal artery. Conversely, localization sensors deployed and adequately in contact with the arterial wall will exhibit some translational movement as the arterial wall distends with each pressure pulse, but the rotational component will be blunted. Thus, proper contact with the arterial wall is ensured, thereby reducing the risk of adverse complications when electrode wall contact is not monitored.

The electrode assembly 90 described above may be used for renal denervation to treat hypertension. Initially, a dye may be injected into the renal artery while utilizing biplane fluoroscopy or rotational fluoroscopy. Mediguide AngioSurvey 3D Reconstruction may be used to create a three-dimensional model of the renal artery. Once the model has been created, the remaining steps of the procedure may be fluoroless, thereby limiting the exposure to fluoroscopy when compared to conventional methods where fluoroscopy is used throughout the procedure.

Following construction of the renal artery model, the electrode assembly may be introduced into the renal artery using the localization sensors 100 projected onto the three-dimensional model as a guide on a visual display. The electrode assembly 90 may be introduced into the body in the collapsed condition, such as, for example, that shown in FIG. 10A, using a transfemoral or other suitable approach. Electrode assembly 90 may be advanced until reaching the ostium of the renal artery. One or more localization sensors 100 may be used to facilitate advancing the assembly 90 into the renal artery so that it is positioned at a point slightly proximal of the renal artery bifurcation.

The physician may then radially expand arms 64 into the expanded condition (FIG. 10B) while using localization sensors 100 and visual displays as described above to ensure proper positioning and orientation within the artery and proper contact of the ablation electrodes 62 with the arterial wall.

A controller (not shown) may be used to provide power to ablate target tissue for a predetermined period of time (e.g., about 15 seconds). A transneural lesion is created across the renal nerves at the ablation electrode 62 to disrupt nerve impulses through the nerves. This step may be performed by simultaneously delivering energy to each of the ablation electrodes 62 or through a quick switching application. The location of each of the localization sensors 100 (and thus the location of each of the ablation electrodes) may be registered and annotated on the three-dimensional model, for example, by changing the color in proximity to the formed lesion. Further information such as time, temperature, total energy delivered, lesion depth and the like may also be encoded by gradations in color, shading or transparency on the visual display. Such information may also be stored and linked to a data table for further analysis.

Following the formation of the first set of lesions, the electrode assembly may be pulled back proximally slightly and positioned for forming a second set of lesions. Visualization of the first set of lesions on the visual display may aid the physician in properly positioning the electrode assembly for forming the second set of lesions. The localization sensor locations upon pulling back the electrode assembly are also rendered on the three-dimensional model. The distance that the catheter was pulled back, any rotation that the catheter has undergone during pullback and other information about the new catheter location in relation to the old location is shown on the visual display. If the distance is not far enough or too far, the physician may be alerted. Moreover, if the rotation is incorrect such that the second set of lesions would overlap with the first set of lesions, the physician may be alerted that an ineffective ablation may be performed. Additionally, icons or graphical indicators may be used to help guide the ablation catheter to the preferred site for the second set of lesions.

Ablation electrode wall contact may be confirmed again via dimensional and motion analysis of the localization sensors. Energy may then be delivered to the ablation electrodes and the location and information such as time, temperature, total energy delivered, lesion depth and the like for forming the second set of lesions may then be encoded by gradations in color, shading or transparency on the visual display. Such information may also be stored and linked to a data table for further analysis.

After forming the desired number of lesions in the renal artery, electrode assembly 90 may be retracted from the ostium of the renal artery. Electrode assembly 90 may then be repositioned in the ostium of the contralateral renal artery and the ablation process repeated. When finished, electrode assembly 90 may be retracted and removed from the patient's body.

Although the systems and methods herein have been described with reference to particular embodiments, it is to be understood that these embodiments are merely illustrative of the principles and applications of the present systems and methods. For example, the foregoing embodiments have illustrated the use of localization sensors in conjunction with radiofrequency ablation electrodes. It will be understood, however, that localization sensors may likewise be used in conjunction with laser-based ablation devices having one more optical fibers disposed within an elongated body and extending longitudinally therethrough. Such optical fibers may be optically coupled to a light source at one end and to a diffuser at another end and configured to focus energy from the light source on target tissue of a blood vessel to ablate the target tissue. For example, the laser energy may be focused on the renal nerves to create lesions therein in the same manner as described above in order to control hypertension in patients. The light source may include a diode laser or a doped fiber laser pumped with a diode laser. It is, therefore, to be understood that numerous modifications may be made to the illustrative embodiments and that other arrangements may be devised without departing from the spirit and scope of the present systems and methods as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. An ablation catheter, comprising:
   an elongated body having a proximal end and a distal end;
   at least one ablation element disposed on the body between the proximal end and the distal end, wherein the ablation element includes a diffuser and an optical fiber having a proximal end and a distal end, the optical fiber being disposed within the elongated body and extending longitudinally therethrough, the proximal end of the optical fiber being optically coupleable to a light source, the diffuser being coupled to the distal end of the optical fiber and configured to focus energy from the light source on target tissue of a blood vessel to ablate the target tissue;

and at least one localization sensor disposed adjacent the at least one ablation element on the body and configured to interact with a magnetic field.

2. The ablation catheter of claim 1, wherein the at least one ablation element is a radiofrequency ablation electrode.

3. The ablation catheter of claim 1, wherein the at least one ablation element includes four ablation elements.

4. The ablation catheter of claim 1, further comprising a plurality of localization sensors.

5. The ablation catheter of claim 1, further comprising a plurality of ablation elements and at least one localization sensor for each of the ablation elements.

6. The ablation catheter of claim 5, wherein each ablation element is a radio frequency ablation electrode, and each localization sensor is disposed under a corresponding one of the ablation electrodes.

7. The ablation catheter of claim 1, wherein each localization sensor is connected to a processor via a wire.

8. The ablation catheter of claim 1, wherein the light source is selected from the group consisting of a diode laser and a doped fiber laser pumped with a diode laser.

9. An ablation catheter, comprising:
a longitudinal rod;
a plurality of arms disposed about the longitudinal rod, and being resiliently biased outwardly away from the longitudinal rod;
at least one ablation element disposed on each of the arms, wherein the ablation element includes a diffuser and an optical fiber having a proximal end and a distal end, the optical fiber being disposed within the elongated body and extending longitudinally therethrough, the proximal end of the optical fiber being optically coupleable to a light source, the diffuser being coupled to the distal end of the optical fiber and configured to focus energy from the light source on target tissue of a blood vessel to ablate the target tissue; and
at least one localization sensor disposed adjacent the at least one ablation element.

10. The ablation catheter of claim 9, wherein the plurality of arms form a collapsible, basket-like arrangement.

11. The ablation catheter of claim 9, wherein the plurality of arms includes four arms arranged circumferentially apart by 90 degrees.

12. The ablation catheter of claim 9, wherein the at least one ablation element is a radiofrequency ablation electrode.

13. A method for ablating vascular tissue, comprising:
introducing into an artery an ablation catheter including an elongated body having a proximal end and a distal end, at least one ablation element disposed on the body between the proximal end and the distal end, and at least one localization sensor disposed on the body adjacent the at least one ablation element;
using the at least one localization sensor to determine an appropriate target tissue for ablation;
ablating the target tissue to provide a therapeutic effect;
displaying a location of the ablation catheter within the artery on a visual display; and
registering locations of a first set of lesions using the at least one localization sensor, computing preferred locations of a second set of lesions based on locations of the first set of lesions using a process, and displaying the preferred locations on the visual display.

14. The method of claim 13, further comprising injecting a dye into the artery, using a visualization technique to create a three-dimensional model of the artery and using the at least one localization sensor to track the ablation catheter through the three-dimensional model.

15. The method of claim 13, wherein the visual display indicates locations of previous ablations.

16. The method of claim 13, further comprising ensuring adequate wall contact between the at least one ablation element and a wall of the artery using the at least one localization sensor.

17. The method of claim 16, wherein the ensuring step includes visual inspection of the ablation element and the wall of the artery.

18. The method of claim 16, wherein the ensuring step includes calculating a distance between the at least one localization sensor and the wall of the artery.

19. The method of claim 16, wherein the ensuring step includes performing motion analysis of the at least one localization sensor.

20. The method of claim 13, wherein the artery is a renal artery.

21. The method of claim 13, wherein the ablating step includes ablating tissue in the renal artery to treat hypertension.

* * * * *